US005843642A

United States Patent [19]

Dmitrovsky et al.

[11] Patent Number: 5,843,642

[45] Date of Patent: Dec. 1, 1998

[54] METHODS FOR DETECTION OF ACUTE PROMYELOCYTIC LEUKEMIA (APL)

[75] Inventors: Ethan Dmitrovsky; Raymond P. Warrell, Jr.; Wilson H. Miller, Jr., all of New York; Stanley Frankel, Amherst, all of N.Y.

[73] Assignee: Sloan-Kettering Institute for Cancer Research, New York, N.Y.

[21] Appl. No.: 95,728

[22] Filed: Jul. 21, 1993

Related U.S. Application Data

[63] Continuation-in-part of Ser. No. 675,084, Mar. 22, 1991, abandoned, and Ser. No. 673,838, Mar. 22, 1991, abandoned.

[51] Int. Cl.[6] .............................. C12Q 1/68; C12P 19/34

[52] U.S. Cl. .......................... 435/6; 435/91.2; 435/91.51; 436/63; 436/64; 436/813; 935/77; 935/78

[58] Field of Search ............................... 435/6, 91.2, 7.1, 435/7.9, 7.8, 91.21, 91.51; 436/64, 63, 813; 935/77, 78; 536/24.31, 24.33, 23.5

[56] References Cited

U.S. PATENT DOCUMENTS 4,681,840 7/1987 Stephenson et al. ....................... 435/6
4,683,195 7/1987 Mullis et al. .............................. 435/6

OTHER PUBLICATIONS de The et al (1990) Nature 347: 558–561.

Castaighe et al (1990) 76: 1704–1709, Blood.

Borrow et al Science (1990) 249:1577–1580.

Biondi, A., et al. (1991) RAR–a Gene Rearrangements as a Genetic Marker for Diagnosis and Monitoring in Acute Promyelocytic Leukemia, *Blood,* vol. 77, No. 7 pp. 1418–1422.

Borrow, J., et al. (1990) Molecular Analysis of Acute Promyelocytic Leukemia Breakpoint Cluster Region on Chromosome 17. *Science,* 249:1577–1580.

Chomienne, C., et al. (1990) The Retinoic Acid Receptor a gene is Rearranged in Retinoic Acid–Sensitive Promyelocytic Leukemias. *Leukemia,* vol. 4, No. 12, pp. 802–807.

de The, et al. (1990) The t(15;17) Translocation of Acute Promyelocytic Leukemia Fuses the Retinoic Acid Receptor a Gene to a Nevel Transcribed Locus. *Nature,* vol. 347, pp. 558–561.

Kumar, et al. (1989) The Technique of Polymerase Chain Reaction. *Technique,* 1(3):133–152.

Lemons, R.S., et al. (1990) Cloning and Characterization of the t(15;17) Translocation Breakpoint Region in Acute Promyelocytic Leukemia. *Genes, Chromosomes and Cancer,* 2:79–87.

Longo, L., et al. (1990) Rearrangements and Aberrant Expression of the Retinoic Acid Receptor a Gene in Acute Promyelocytic Leukemias. *J. Exp. Med.* 172:1571–1575.

Longo, L., et al. (1990) Mapping of Chromosome 17 breakpoints in Acute Myeloi Leukemias. *Oncogne,* 5:1557–1563.

Memorial Sloan–Kettering Cancer Center Newsletter, (1991) Pioneering Study Links New Therapy to Gene Damage Site, *Center News,* pp. 1 and 4.

(List continued on next page.)

*Primary Examiner*—Carla J. Myers
*Attorney, Agent, or Firm*—John P. White

[57] ABSTRACT

The present invention provides a method of diagnosing APL in a subject which comprises detecting in a sample from the subject either nucleic acid encoding an abnormal RAR-α receptor or an expressed protein encoded thereby. The present invention also provides methods of identifying a subject with APL who will or will not respond to treatment with a retinoid, as well as a subjects with APL who do not express a detectable t(15;17) translocation but will or will not respond to treatment with a retinoid. In addition, the present invention provides methods for monitoring the activity of APL and the process of treatment of APL. The present invention provides methods of identifying a subject with a neoplastic condition other than APL who will or will not respond to treatment with a retinoid as well as methods for monitoring the level of disease activity and progress and adequacy of treatment of a neoplastic condition. Lastly, the present invention provides a method for inhibiting the growth of a neoplastic cell.

20 Claims, 12 Drawing Sheets

OTHER PUBLICATIONS

Miller, Jr., et al. (Dec. 1990) Novel Retinoic Acid Receptor—a Transcripts in Acute Promyelocytic Leukemia Responsive to All–Trans–Retinoic Acid. *J. Natl. Cancer Inst.,* 82(24):1932–1933.

Warrell Jr., et al. (May 16, 1991) Differentiation Therapy of Acute Promyelocytic Leukemia with Tretinoin (All–Trans–Retinoic Acid). *New England Journal of Medicine,* 324:1385–1393.

Warrell Jr., et al. (1991) All Trans Retinoic Acid in Acute Promyelocytic Leukemia: Preliminary U.S. Clinical Experience. *Blood* (*Suppl.*), 76:334A.

Zabel, B., et al. (1983) High–Resolution Chromosomal Localization of Human Genes for Amylase, Proopiomelanocortin, Somatostatin, and a DNA Fragment (D3sl) by in situ Hybridization. Proc. Natl. Acad. Sci. U.S.A., 80:6932–6936.

```
CTCCCCTTCA GCTTCTCTTC ACGCACTCCA AGATCTAAAC CGAGAATCGA AACTAAGCTG      60

GGGTCC ATG GAG CCT GCA CCC GCC CGA TCT CCG AGG CCC CAG CAG GAC      108
       Met Glu Pro Ala Pro Ala Arg Ser Pro Arg Pro Gln Gln Asp
        1               5                  10

CCC GCC CGG CCC CAG GAG CCC ACC ATG CCT CCC CCC GAG ACC CCC TCT      156
Pro Ala Arg Pro Gln Glu Pro Thr Met Pro Pro Pro Glu Thr Pro Ser
 15                  20                  25                  30

GAA GGC CGC CAG CCC AGC CCC AGC CCC AGC CCT ACA GAG CGA GCC CCC      204
Glu Gly Arg Gln Pro Ser Pro Ser Pro Ser Pro Thr Glu Arg Ala Pro
                 35                  40                  45

GCT TCG GAG GAG GAG TTC CAG TTT CTG CGC TGC CAG CAA TGC CAG GCG      252
Ala Ser Glu Glu Glu Phe Gln Phe Leu Arg Cys Gln Gln Cys Gln Ala
             50                  55                  60

GAA GCC AAG TGC CCG AAG CTG CTG CCT TGT CTG CAC ACG CTG TGC TCA      300
Glu Ala Lys Cys Pro Lys Leu Leu Pro Cys Leu His Thr Leu Cys Ser
         65                  70                  75

GGA TGC CTG GAG GCG TCG GGC ATG CAG TGC CCC ATC TGC CAG GCG CCC      348
Gly Cys Leu Glu Ala Ser Gly Met Gln Cys Pro Ile Cys Gln Ala Pro
     80                  85                  90

TGG CCC CTA GGT GCA GAC ACA CCC GCC CTG GAT AAC GTC TTT TTC GAG      396
Trp Pro Leu Gly Ala Asp Thr Pro Ala Leu Asp Asn Val Phe Phe Glu
 95                 100                 105                 110

AGT CTG CAG CGG CGC CTG TCG GTG TAC CGG CAG ATT GTG GAT GCG CAG      444
Ser Leu Gln Arg Arg Leu Ser Val Tyr Arg Gln Ile Val Asp Ala Gln
                115                 120                 125
```

FIG. 4B

```
GCT GTG TGC ACC CGC TGC AAA GAG TCG GCC GAC TTC TGG TGC TTT GAG    492
Ala Val Cys Thr Arg Cys Lys Glu Ser Ala Asp Phe Trp Cys Phe Glu
            130                 135                 140

TGC GAG CAG CTC CTC TGC GCC AAG TGC TTC GAG GCA CAC CAG TGG TTC    540
Cys Glu Gln Leu Leu Cys Ala Lys Cys Phe Glu Ala His Gln Trp Phe
        145                 150                 155

CTC AAG CAC GAG GCC CGG CCC CTA GCA GAG CTG CGC AAC CAG TCG GTG    588
Leu Lys His Glu Ala Arg Pro Leu Ala Glu Leu Arg Asn Gln Ser Val
    160                 165                 170

CGT GAG TTC CTG GAC GGC ACC CGC AAG ACC AAC AAC ATC TTC TGC TCC    636
Arg Glu Phe Leu Asp Gly Thr Arg Lys Thr Asn Asn Ile Phe Cys Ser
175                 180                 185                 190

AAC CCC AAC CAC CGC ACC CCT ACG CTG ACC AGC ATC TAC TGC CGA GGA    684
Asn Pro Asn His Arg Thr Pro Thr Leu Thr Ser Ile Tyr Cys Arg Gly
                195                 200                 205

TGT TCC AAG CCG CTG TGC TGC TCG TGC GCG CTC CTT GAC AGC AGC CAC    732
Cys Ser Lys Pro Leu Cys Cys Ser Cys Ala Leu Leu Asp Ser Ser His
            210                 215                 220

AGT GAG CTC AAG TGC GAC ATC AGC GCA GAG ATC CAG CAG CGA CAG GAG    780
Ser Glu Leu Lys Cys Asp Ile Ser Ala Glu Ile Gln Gln Arg Gln Glu
        225                 230                 235

GAG CTG GAC GCC ATG ACG CAG GCG CTG CAG GAG CAG GAT AGT GCC TTT    828
Glu Leu Asp Ala Met Thr Gln Ala Leu Gln Glu Gln Asp Ser Ala Phe
    240                 245                 250
```

FIG. 4C

```
GGC GCG GTT CAC GCG CAG ATG CAC GCG GCC GTC GGC CAG CTG GGC CGC     876
Gly Ala Val His Ala Gln Met His Ala Ala Val Gly Gln Leu Gly Arg
255                 260                     265                 270

GCG CGT GCC GAG ACC GAG GAG CTG ATC CGC GAG CGC GTG CGC CAG GTG     924
Ala Arg Ala Glu Thr Glu Glu Leu Ile Arg Glu Arg Val Arg Gln Val
                275                 280                 285

GTA GCT CAC GTG CGG GCT CAG GAG CGC GAG CTG CTG GAG GCT GTG GAC     972
Val Ala His Val Arg Ala Gln Glu Arg Glu Leu Leu Glu Ala Val Asp
            290                 295                 300

GCG CGG TAC CAG CGC GAC TAC GAG GAG ATG GCC AGT CGG CTG GGC CGC    1020
Ala Arg Tyr Gln Arg Asp Tyr Glu Glu Met Ala Ser Arg Leu Gly Arg
        305                 310                 315

CTG GAT GCT GTG CTG CAG CGC ATC CGC ACG GGC AGC GCG CTG GTG CAG    1068
Leu Asp Ala Val Leu Gln Arg Ile Arg Thr Gly Ser Ala Leu Val Gln
    320                 325                 330

AGG ATG AAG TGC TAC GCC TCG GAC CAG GAG GTG CTG GAC ATG CAC GGT    1116
Arg Met Lys Cys Tyr Ala Ser Asp Gln Glu Val Leu Asp Met His Gly
335                 340                     345                 350

TTC CTG CGC CAG GCG CTC TGC CGC CTG CGC CAG GAG GAG CCC CAG AGC    1164
Phe Leu Arg Gln Ala Leu Cys Arg Leu Arg Gln Glu Glu Pro Gln Ser
                355                 360                 365
```

FIG. 4D

```
CTG CAA GCT GCC GTG CGC ACC GAT GGC TTC GAC GAG TTC AAG GTG CGC    1212
Leu Gln Ala Ala Val Arg Thr Asp Gly Phe Asp Glu Phe Lys Val Arg
            370                 375                 380

CTG CAG GAC CTC AGC TCT TGC ATC ACC CAG GGG AAA GCC ATT GAG ACC    1260
Leu Gln Asp Leu Ser Ser Cys Ile Thr Gln Gly Lys Ala Ile Glu Thr
        385                 390                 395

CAG AGC AGC AGT TCT GAA GAG ATA GTG CCC AGC CCT CCC TCG CCA CCC    1308
Gln Ser Ser Ser Ser Glu Glu Ile Val Pro Ser Pro Pro Ser Pro Pro
    400                 405                 410

CCT CTA CCC CGC ATC TAC AAG CCT TGC TTT GTC TGT CAG GAC AAG TCC    1356
Pro Leu Pro Arg Ile Tyr Lys Pro Cys Phe Val Cys Gln Asp Lys Ser
415                 420                 425                 430

TCA GGC TAC CAC TAT GGG GTC AGC GCC TGT GAG GGC TGC AAG GGC TTC    1404
Ser Gly Tyr His Tyr Gly Val Ser Ala Cys Glu Gly Cys Lys Gly Phe
                435                 440                 445

TTC CGC CGC AGC ATC CAG AAG AAC ATG GTG TAC ACG TGT CAC CGG GAC    1452
Phe Arg Arg Ser Ile Gln Lys Asn Met Val Tyr Thr Cys His Arg Asp
            450                 455                 460

AAG AAC TGC ATC ATC AAC AAG GTG ACC CGG AAC CGC TGC CAG TAC TGC    1500
Lys Asn Cys Ile Ile Asn Lys Val Thr Arg Asn Arg Cys Gln Tyr Cys
        465                 470                 475

CGA CTG CAG AAG TGC TTT GAA GTG GGC ATG TCC AAG GAG TCT GTG AGA    1548
Arg Leu Gln Lys Cys Phe Glu Val Gly Met Ser Lys Glu Ser Val Arg
    480                 485                 490
```

FIG. 4E

```
AAC GAC CGA AAC AAG AAG AAG AAG GAG GTG CCC AAG CCC GAG TGC TCT    1596
Asn Asp Arg Asn Lys Lys Lys Lys Glu Val Pro Lys Pro Glu Cys Ser
495                 500                 505                 510

GAG AGC TAC ACG CTG ACG CCG GAG GTG GGG GAG CTC ATT GAG AAG GTG    1644
Glu Ser Tyr Thr Leu Thr Pro Glu Val Gly Glu Leu Ile Glu Lys Val
                515                 520                 525

CGC AAA GCG CAC CAG GAA ACC TTC CCT GCC CTC TGC CAG CTG GGC AAA    1692
Arg Lys Ala His Gln Glu Thr Phe Pro Ala Leu Cys Gln Leu Gly Lys
            530                 535                 540

TAC ACT ACG AAC AAC AGC TCA GAA CAA CGT GTC TCT CTG GAC ATT GAC    1740
Tyr Thr Thr Asn Asn Ser Ser Glu Gln Arg Val Ser Leu Asp Ile Asp
        545                 550                 555

CTC TGG GAC AAG TTC AGT GAA CTC TCC ACC AAG TGC ATC ATT AAG ACT    1788
Leu Trp Asp Lys Phe Ser Glu Leu Ser Thr Lys Cys Ile Ile Lys Thr
    560                 565                 570

GTG GAG TTC GCC AAG CAG CTG CCC GGC TTC ACC ACC CTC ACC ATC GCC    1836
Val Glu Phe Ala Lys Gln Leu Pro Gly Phe Thr Thr Leu Thr Ile Ala
575                 580                 585                 590

GAC CAG ATC ACC CTC CTC AAG GCT GCC TGC CTG GAC ATC CTG ATC CTG    1884
Asp Gln Ile Thr Leu Leu Lys Ala Ala Cys Leu Asp Ile Leu Ile Leu
                595                 600                 605

CGG ATC TGC ACG CGG TAC ACG CCC GAG CAG GAC ACC ATG ACC TTC TCG    1932
Arg Ile Cys Thr Arg Tyr Thr Pro Glu Gln Asp Thr Met Thr Phe Ser
            610                 615                 620
```

FIG. 4F

```
GAC GGG CTG ACC CTG AAC CGG ACC CAG ATG CAC AAC GCT GGC TTC GGC      1980
Asp Gly Leu Thr Leu Asn Arg Thr Gln Met His Asn Ala Gly Phe Gly
        625                 630                 635

CCC CTC ACC GAC CTG GTC TTT GCC TTC GCC AAC CAG CTG CTG CCC CTG      2028
Pro Leu Thr Asp Leu Val Phe Ala Phe Ala Asn Gln Leu Leu Pro Leu
    640                 645                 650

GAG ATG GAT GAT GCG GAG ACG GGG CTG CTC AGC GCC ATC TGC CTC ATC      2076
Glu Met Asp Asp Ala Glu Thr Gly Leu Leu Ser Ala Ile Cys Leu Ile
655                 660                 665                 670

TGC GGA GAC CGC CAG GAC CTG GAG CAG CCG GAC CGG GTG GAC ATG CTG      2124
Cys Gly Asp Arg Gln Asp Leu Glu Gln Pro Asp Arg Val Asp Met Leu
                675                 680                 685

CAG GAG CCG CTG CTG GAG GCG CTA AAG GTC TAC GTG CGG AAG CGG AGG      2172
Gln Glu Pro Leu Leu Glu Ala Leu Lys Val Tyr Val Arg Lys Arg Arg
            690                 695                 700

CCC AGC CGC CCC CAC ATG TTC CCC AAG ATG CTA ATG AAG ATT ACT GAC      2220
Pro Ser Arg Pro His Met Phe Pro Lys Met Leu Met Lys Ile Thr Asp
        705                 710                 715

CTG CGA AGC ATC AGC GCC AAG GGG GCT GAG CGG GTG ATC ACG CTG AAG      2268
Leu Arg Ser Ile Ser Ala Lys Gly Ala Glu Arg Val Ile Thr Leu Lys
    720                 725                 730

ATG GAG ATC CCG GGC TCC ATG CCG CCT CTC ATC CAG GAA ATG TTG GAG      2316
Met Glu Ile Pro Gly Ser Met Pro Pro Leu Ile Gln Glu Met Leu Glu
735                 740                 745                 750
```

FIG. 4G

```
AAC TCA GAG GGC CTG GAC ACT CTG AGC GGA CAG CCG GGG GGT GGG GGG     2364
Asn Ser Glu Gly Leu Asp Thr Leu Ser Gly Gln Pro Gly Gly Gly Gly
                755                 760                 765

CGG GAC GGG GGT GGC CTG GCC CCC CCG CCA GGC AGC TGT AGC CCC AGC     2412
Arg Asp Gly Gly Gly Leu Ala Pro Pro Pro Gly Ser Cys Ser Pro Ser
            770                 775                 780

CTC AGC CCC AGC TCC AAC AGA AGC AGC CCG GCC ACC CAC TCC CCG         2457
Leu Ser Pro Ser Ser Asn Arg Ser Ser Pro Ala Thr His Ser Pro
        785                 790                 795

TGACCGCCCA CGCCACATGG ACACAGCCCT CGCCCTCCGC CCCGGCTTTT CTCTGCCTTT   2517

CTACCGACCA TGTGACCCCG CACCAGCCCT GCCCCCACCT GCCCTCCCGG GCAGTACTGG   2577

GGACCTTCCC TGGGGGACGG GGAGGGAGGA GGCAGCGACT CCTTGGACAG AGGCCTGGGC   2637

CCTCAGTGGA CTGCCTGCTC CCACAGCCTG GGCTGACGTC AGAGGCCGAG GCCAGGAACT   2697

GAGTGAGGCC CCTGGTCCTG GGTCTCAGGA TGGGTCCTGG GGGCCTCGTG TTCATCAAGA   2757

CACCCCTCTG CCCAGCTCAC CACATCTTCA TCACCAGCAA ACGCCAGGAC TTGGCTCCCC   2817

CATCCTCAGA ACTCACAAGC CATTGCTCCC CAGCTGGGGA ACCTCAACCT CCCCCCTGCC   2877

TCGGTTGGTG ACAGAGGGGG TGGGACAGGG GCGGGGGGTT CCCCCTGTAC ATACCCTGCC   2937

ATACCAACCC CAGGTATTAA TTCTCGCTGG TTTTGTTTTT ATTTTAATTT TTTTGTTTTG   2997

ATTTTTTTAA TAAGAATTTT CATTTTAAGC AAAAAAAAA                          3036
```

METHODS FOR DETECTION OF ACUTE PROMYELOCYTIC LEUKEMIA (APL)

This application is a continuation-in-part of U.S. Ser. No. 07/675,084, filed Mar. 22, 1991 abandoned and U.S. Ser. No. 07/673,838, filed Mar. 22, 1991, abandoned, the contents of which are hereby incorporated by reference.

The invention described herein was made in part in the course of work under grant FD-R-000674 from the Food and Drug Administration, Department of Health and Human Services and grant CA-09207-14 from the National Cancer Institute. The U.S. Government has certain rights in this invention.

BACKGROUND OF THE INVENTION

Throughout this application, various publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

Acute promyelocytic leukemia (APL) comprises approximately 15% of the adult acute non-lymphoblastic leukemias (1). The disease is associated with a specific cytogenetic abnormality, the translocation of a portion of the long arm of chromosome 17 onto the long arm of chromosome 15[t (15;17)(q21;q11–22)] (2). Recently, several important discoveries have been made in this disease. The breakpoint region for the chromosome 17 translocation has been cloned (3) and molecular studies have revealed DNA rearrangements that clustered in the region of the first intron for the nuclear retinoic acid receptor-alpha (RAR-α)(4,5). The inventors and others have shown that this rearrangement resulted in the expression of abnormal mRNA RAR-α transcripts (6–8). These findings were of special interest since RAR-α was previously shown to be involved in the growth and differentiation of certain myeloid cells in vitro (9).

Prior to these laboratory developments, investigators in China and France reported that treatment with all-trans retinoic acid induced complete remission in patients with acute promyelocytic leukemia (10,11). Together, these findings suggested to the inventors a possible molecular link between the pathogenesis of this malignant disease and its treatment.

To further explore the nature of this clinical response, a study was conducted using all-trans retinoic acid in patients with acute promyelocytic leukemia (26,35). In that study, the inventors confirmed that a high proportion of patients treated with all-trans retinoic acid achieved complete remission, and that this beneficial effect was achieved with quite low morbidity. The inventors also found that patients with acute promyelocytic leukemia who responded to this drug consistently expressed abnormal mRNA transcripts for RAR-α, suggesting that this rearranged receptor was a molecular target of the treatment. For the first time, it was shown that expression of the abnormal message markedly decreased following clinical response. However, aberrant mRNA transcripts could still be detected in some patients after remission had been documented by conventional morphologic and cytogenetic criteria.

The inventors have thus shown that this abnormality is a sensitive and specific diagnostic marker for patients with APL who will respond to this non-toxic therapy. Conversely, patients with APL who lack this marker can be prospectively identified such that alternative treatment can be used. Finally, the inventors have documented the presence of aberrant RAR-α receptor in malignant diseases other than APL, thereby identifying a substantial number of patients who could benefit from preventive or therapeutic use of a retinoid compound.

SUMMARY OF THE INVENTION

The present invention provides a method of diagnosing APL in a subject which comprises detecting in a sample from the subject either nucleic acid encoding an abnormal RAR-α receptor or an expressed protein encoded thereby.

The present invention also provides a method of identifying a subject with APL who will respond to treatment with a retinoid which comprises detecting in a sample from the subject either nucleic acid encoding an abnormal RAR-α receptor or an expressed protein encoded thereby.

The present invention also provides a method of identifying a subject with APL who will not respond to treatment with a retinoid which comprises detecting in a sample from the subject the absence of nucleic acid encoding an abnormal RAR-α receptor or an expressed protein encoded thereby.

The present invention further provides a method of identifying a subject with APL who does not express a detectable t(15;17) translocation but will respond to treatment with a retinoid which comprises detecting in a sample from the subject either nucleic acid encoding an abnormal RAR-α receptor or an expressed protein encoded thereby.

The present invention even further provides a method of identifying a subject with APL who does not express a detectable t(15;17) translocation and will not respond to treatment with a retinoid which comprises detecting in a sample from the subject the absence of nucleic acid encoding an abnormal RAR-α receptor or an expressed protein encoded thereby.

In addition, the present invention provides a method for monitoring the level of disease activity in a subject who has received treatment for APL which comprises monitoring the level of nucleic acid encoding an abnormal RAR-α receptor or an expressed protein encoded thereby at various stages of treatment.

The present invention also provides a method for monitoring the progress and adequacy of treatment in a subject who has received treatment for APL which comprises monitoring the level of nucleic acid encoding an abnormal RAR-α receptor or an expressed protein encoded thereby at various stages of treatment.

The present invention provides a method of identifying a subject with a neoplastic condition other than APL who will respond to treatment with a retinoid which comprises detecting in a sample from the subject either nucleic acid encoding an abnormal RARα receptor or an expressed protein encoded thereby.

The present invention also provides a method of identifying a subject with a neoplastic condition other than APL who will not respond to treatment with a retinoid which comprises detecting in a sample from the subject the absence of nucleic acid encoding an abnormal RAR-α receptor or an expressed protein encoded thereby.

The present invention further provides a method for monitoring the level of disease activity in a subject who has received treatment for a neoplastic condition which comprises monitoring the level of nucleic acid encoding an abnormal RAR-α receptor or an expressed protein encoded thereby at various stages of treatment.

The present invention still further provides a method for monitoring the progress and adequacy of treatment in a subject who has received treatment for a neoplastic condition which comprises monitoring the level of nucleic acid encoding an abnormal RAR-α receptor or an expressed protein encoded thereby at various stages of treatment.

Lastly, the present invention provides a method of inhibiting the growth of a neoplastic cell wherein the cell is characterized by the presence of an abnormal RAR-α receptor which comprises contacting an antibody which specifically recognizes an expressed protein encoding an RAR-α receptor conjugated to a therapeutic agent under suitable conditions so that an antibody-antigen complex is formed, thereby inhibiting the growth of the neoplastic cell.

BRIEF DESCRIPTION OF THE FIGURES

FIGS. 4A–4G: Nucleic acid sequence and deduced amino acid sequence of a myl/RARα fusion product SEQ ID NO: 1. The sequences on which specific PCR primers were based are underlined (e.g., between nucleotides 715–744, 975–1001, and 1382–1413, inclusive).

DETAILED DESCRIPTION OF THE INVENTION

Figure 1A:
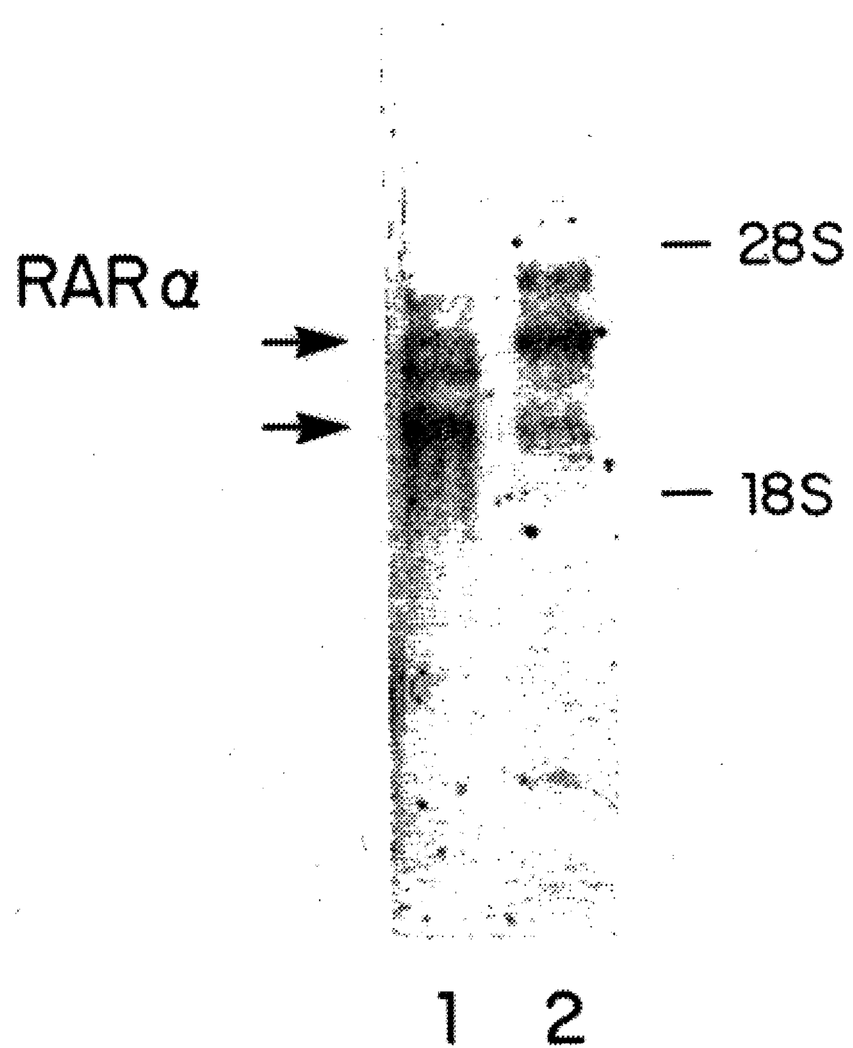
FIGS. 1A and 1B: A) Northern blot analysis for RAR-α mRNA expression in patients with acute promyelocytic leukemia. Two patterns of aberrant expression are depicted. The arrows depict the position of the normal RAR-α mRNA species. Lane 1 represents total cellular RNA purified from bone marrow mononuclear cells of patient 2 and demonstrates two novel RAR-α bands. Lane 2 from Patient 3 contains a single aberrant band. B) Sequential Northern analyses of RAR-α mRNA in leukemic cells from Patient 7. Expression of the abnormal species decreases from treatment day 7 (Lane 1) to the time of complete remission on day 46 (Lane 2) after treatment with all-trans retinoic acid. The relative signal intensity of the abnormal species decreases compared to the two normal bands.

The present invention provides a method of diagnosing APL in a subject which comprises detecting in a sample from the subject either nucleic acid encoding an abnormal RAR-α receptor or an expressed protein encoded thereby.

The term "subject" includes, but is not limited to, animals and human beings. The term "sample" includes, but is not limited to, cells tissue, bone marrow, and biological fluid serum such as plasma and cerebral spinal fluid. The sample is removed from the subject by techniques clearly known to those skilled in the art.

In one embodiment of the present invention, nucleic acid encoding an abnormal RAR-α receptor is detected by size fractionation. The size fractionation may be effected by a polyacrylamide gel, agarose gel, or any other type of polymerized gel.

In another embodiment, the detection of nucleic acid encoding an abnormal RAR-α receptor comprises contacting the nucleic acid from the sample with an RAR-α probe labeled with a detectable marker under conditions permitting the RAR-α probe to hybridize with nucleic acid encoding the abnormal RAR-α receptor, detecting hybridization of nucleic acid encoding the abnormal RAR-α receptor with the probe, and thereby detecting the presence of nucleic acid encoding the abnormal RAR-α receptor.

The nucleic acid from the sample may be isolated by techniques clearly known to those skilled in the art and includes, but is not limited to, DNA extraction and ethanol precipitation (69). The nucleic acid my be DNA or RNA and depending on which one, one skilled in the art would know how to carry out the hybridization. The detectable marker includes but is not limited to the following markers: a radiolabelled molecule, a fluorescent molecule, an enzyme or a ligand.

In yet another embodiment, the detection of nucleic acid encoding an abnormal RAR-α receptor comprises contacting nucleic acid from the sample with one or more primers comprising a portion of the t(15;17) translocation under conditions for polymerase chain reaction so as to amplify nucleic acid encoding the abnormal RAR-α receptor, detecting amplified nucleic acid encoding the abnormal RAR-α receptor, and thereby detecting nucleic acid encoding the abnormal RAR-α receptor.

The polymerase chain reaction is performed by techniques clearly known by those skilled in the art (61–64, 69).

The amplified nucleic acid encoding the abnormal RAR-α receptor may be detected by size fractionation. The size fractionated material can then be assayed for the presence of sequences having appropriate size based on the distance between the primers employed for amplification. The size fractionation may be effected by a polyacrylamide gel, agarose gel, or any other type of polymerized gel.

The amplified nucleic acid encoding the abnormal RAR-α receptor may also be detected by contacting the amplified nucleic acid encoding the abnormal RAR-α receptor with an RAR-α probe labeled with a detectable marker under conditions permitting the RAR-α probe to hybridize with amplified nucleic acid encoding the abnormal RAR-α receptor, detecting hybridization of amplified nucleic acid encoding the abnormal RAR-α receptor with the probe, and thereby detecting nucleic acid encoding the abnormal RAR-α receptor.

The detectable marker may be but is not limited to the following markers: a radiolabelled molecule, a fluorescent molecule, an enzyme, or a ligand.

In one embodiment of the present invention, the expressed protein is detected by Western blotting. In another embodiment, the expressed protein is detected by immunoprecipitation.

The present invention also provides a method of identifying a subject with APL who will respond to treatment with a retinoid which comprises detecting in a sample from the subject either nucleic acid encoding an abnormal RAR-α receptor or an expressed protein encoded thereby. Preferably, the retinoid is trans-retinoic acid.

The means for detection of nucleic acid encoding an abnormal RAR-α receptor or an expressed protein encoded thereby are the same as described previously.

The present invention also provides a method of identifying a subject with APL who will not respond to treatment with a retinoid which comprises detecting in a sample from the subject the absence of nucleic acid encoding an abnormal RAR-α receptor or an expressed protein encoded thereby. One example of a retinoid is all-trans-retinoic acid. However, any retinoid may be used for treatment.

The term "subject" includes, but is not limited to, animals and human beings. The term "sample" includes, but is not limited to, cells, tissue, bone marrow, and biological fluid serum such as plasma and cerebral spinal fluid. The sample is removed from the subject by techniques clearly known to those skilled in the art.

In one embodiment of the present invention, the absence of nucleic acid encoding an abnormal RAR-α receptor is detected by size fractionation. The size fractionation may be effected by a polyacrylamide gel, agarose gel, or any other type of polymerized gel.

In another embodiment, the detection of the absence of nucleic acid encoding an abnormal RAR-α receptor comprises contacting nucleic acid from the sample with an RAR-α probe labeled with a detectable marker under conditions permitting the RAR-α probe to hybridize with nucleic acid encoding the abnormal RAR-α receptor, detecting the absence of hybridization of nucleic acid encoding the abnormal receptor with the probe, and thereby detecting the absence of nucleic acid encoding the abnormal RAR-α receptor.

The polymerase chain reaction is performed by techniques clearly known by those skilled in the art (61–64).

The nucleic acid from the sample may be isolated by techniques clearly known to those skilled in the art and includes, but is not limited to, DNA extraction and ethanol precipitation (69). The nucleic acid may be DNA or RNA and depending on which one, one skilled in the art would know how to carry out the hybridization. The detectable marker includes but is not limited to the following markers: a radiolabelled molecule, a fluorescent molecule, an enzyme or a ligand.

In yet another embodiment, the detection of nucleic acid encoding an abnormal RAR-α receptor comprises contacting nucleic acid from the sample with one or more primers comprising a portion of the t(15;17) translocation under conditions for polymerase chain reaction so as to permit amplification of nucleic acid encoding the abnormal RAR-α receptor, detecting the absence of amplified nucleic acid encoding the abnormal RAR-α receptor, and thereby detecting the absence of nucleic acid encoding the abnormal RAR-α receptor.

The expressed protein is isolated from the sample using techniques clearly known to those skilled in the art. In one embodiment of the present invention, the absence of the expressed protein is detected by Western blotting. In another embodiment, the absence of the expressed protein is detected by immunoprecipitation.

In the preferred embodiment, the polymerase chain reaction is effected by reverse transcriptase polymerase chain reaction.

In one embodiment of the present invention, the absence of the expressed protein is detected by Western blotting. In another embodiment, the absence of the expressed protein is detected by immunoprecipitation.

The present invention also provides a method of identifying a subject with APL who does not express a detectable t(15;17) translocation but will respond to treatment with a retinoid which comprises detecting in a sample from the subject either nucleic acid encoding an abnormal RAR-α receptor or an expressed protein encoded thereby.

A subject with APL who does not express a detectable t(15;17) translocation as stated hereinabove and the following paragraphs means that the t(15;17) translocation is not detectable by conventional cytogenetics.

The methods for detection of nucleic acid encoding an abnormal RAR-α receptor or an expressed protein encoded thereby are the same as described previously.

The present invention also provides a method of identifying a subject with APL who does not express a detectable t(15;17) translocation and will not respond to treatment with a retinoid which comprises detecting in a sample from the subject the absence of nucleic acid encoding an abnormal RAR-α receptor or an expressed protein encoded thereby.

The means for detection of the absence of nucleic acid encoding an abnormal RAR-α receptor or an expressed protein encoded thereby are the same as described previously.

The present invention further provides a method for monitoring the level of disease activity in a subject who has received treatment for APL which comprises monitoring the level of nucleic acid encoding an abnormal RAR-α receptor or an expressed protein encoded thereby at various stages of treatment.

The level of nucleic acid encoding an abnormal RAR-α receptor may be monitored using techniques for detection of RAR-α as described previously. Preferably, the level of nucleic acid may be monitored using Northern blot analysis by comparing and quantitating the relevant contributions of both the normal and aberrant responses. Alternatively, competitive PCR may be used to quantitate the levels of nucleic acid (62).

The present invention still further provides a method for monitoring the progress and adequacy of treatment in a subject who has received treatment for APL which comprises monitoring the level of nucleic acid encoding an abnormal RAR-α receptor or an expressed protein encoded thereby at various stages of treatment.

The level of nucleic acid encoding an abnormal RAR-α receptor may be monitored using techniques for detection and monitoring of RAR-α as described previously.

In addition, the present invention provides a method of identifying a subject with a neoplastic condition other than APL who will respond to treatment with a retinoid which comprises detecting in a sample from the subject either nucleic acid encoding an abnormal RAR-α receptor or an expressed protein encoded thereby.

In one embodiment of the present invention, the neoplastic condition is lung cancer. In another embodiment, the neoplastic condition is breast cancer. One example of a retinoid is all-trans-retinoic acid. However, any retinoid may be used for treatment. The means for detection of nucleic acid encoding an abnormal RAR-α receptor or an expressed protein encoded thereby are the same as described previously.

The present invention also provides a method of identifying a subject with a neoplastic condition other than APL who will not respond to treatment with a retinoid which comprises detecting in a sample from the subject the absence of nucleic acid encoding an abnormal RAR-α receptor or an expressed protein encoded thereby.

In one embodiment of the present invention, the neoplastic condition is lung cancer. In another embodiment, the neoplastic condition is breast cancer. One example of a retinoid is all-trans-retinoic acid. However, any retinoid may be used for treatment. The means for detection of nucleic acid encoding an abnormal RAR-α receptor or an expressed protein encoded thereby are the same as described previously.

The present invention also provides a method for monitoring the level of disease activity in a subject who has received treatment for a neoplastic condition which comprises monitoring the level of nucleic acid encoding an abnormal RAR-α receptor or an expressed protein encoded thereby at various stages of treatment.

The level of nucleic acid encoding an abnormal RAR-α receptor may be monitored using techniques for detection and monitoring of RAR-α as described previously.

The present invention further provides a method for monitoring the progress and adequacy of treatment in a subject who has received treatment for a neoplastic condition which comprises monitoring the level of nucleic acid encoding an abnormal RAR-α receptor or an expressed protein encoded thereby at various stages of treatment.

The level of nucleic acid encoding an abnormal RAR-α receptor may be monitored using techniques for detection and monitoring of RAR-α as described previously.

Lastly, the present invention further provides a method of inhibiting the growth of a neoplastic cell wherein the cell is characterized by the presence of an abnormal RAR-α receptor which comprises contacting an antibody which specifically recognizes an expressed protein encoding an RAR-α receptor conjugated to a therapeutic agent under suitable conditions so that an antibody-antigen complex is formed, thereby inhibiting the growth of the neoplastic cell.

In one embodiment of the present invention, the neoplastic condition is lung cancer. In another embodiment, the neoplastic condition is breast cancer. The antibody may be polyclonal or monoclonal and derived from murine cells as well as human cells. Preferably, the antibody is derived from human cells. Therapeutic agents include, but are not limited to, a therapeutic agent selected from the group consisting of radioisotopes, cytotoxic compounds, toxins, bacterial toxins, toxoids, and chemotherapeutic agents.

In accordance with the present invention, there is provided a method for the detection of translocation between-chromosomes 15 and 17, wherein the occurrence of said translocation in a subject is indicative of acute promyelocytic leukemia, said method comprising contacting single-stranded nucleic acid sequences derived from said subject with at least one combination of primers selected from:

a) at least one sense primer, wherein sense primer comprises at least 15 contiguous nucleotide bases selected from a portion of the myl-RARα fusion mRNA, wherein said portion is upstream (5') of the point at which the myl-RARα fusion occurs, and at least one anti-sense primer, wherein anti-sense primer comprises at least 15 contiguous nucleotide bases selected from a portion of the myl-RARα fusion mRNA, wherein said portion is downstream (3') of the point at which the myl-RARα fusion occurs; or b) at least one sense primer, wherein sense primer comprises at least 15 contiguous nucleotide bases selected from a portion of the RARα-myl fusion mRNA, wherein said portion is upstream (5') of the point at which the RARα-myl fusion occurs, and at least one anti-sense primer, wherein anti-sense primer comprises at least 15 contiguous nucleotide bases selected from a portion of the RARα-myl fusion mRNA, wherein said portion is downstream (3') of the point at which the RARα-myl fusion occurs; wherein said contacting is carried out under nucleic acid amplification conditions; and thereafter monitoring for the formation of amplified sequences.

In accordance with another embodiment of the present invention, there is provided a composition comprising at least one combination of nucleic acid sequences selected from:

a) at least one sense primer, wherein sense primer comprises at least 15 contiguous nucleotide bases selected from a portion of the myl-RARα fusion mRNA, wherein said portion is upstream (5') of the point at which the myl-RARα fusion occurs, and at least one anti-sense primer, wherein anti-sense primer comprises at least 15 contiguous nucleotide bases selected from a portion of the myl-RARα fusion mRNA, wherein said portion is downstream (3') of the point at which the myl-RARα fusion occurs; or b) at least one sense primer, wherein sense primer comprises at least 15 contiguous nucleotide bases selected from a portion of the RARα-myl fusion mRNA, wherein said portion is upstream (5') of the point at which the RARα-myl fusion occurs, and at least one anti-sense primer, wherein anti-sense primer comprises at least 15 contiguous nucleotide bases selected from a portion of the RARα-myl fusion mRNA, wherein said portion is downstream (3') of the point at which the RARα-myl fusion occurs.

Primers contemplated for use in the practice of the present invention are generally employed in pairs. Thus, there will be employed at least one sense primer from a portion of the myl gene upstream of the point at which translocation between chromosomes 15 and 17 occurs, and at least one anti-sense primer from a portion of the retinoic acid receptor-α (RARα) gene downstream of the point at which translocation occurs. Alternatively (or as a confirmatory pair of primers once amplification has been carried out with the above-described pair of primers), there can be employed at least one sense primer from a portion of the RARα gene upstream of the point at which translocation between chromosomes 15 and 17 occurs, and at least one anti-sense primer from a portion of the myl gene downstream of the point at which translocation between chromosomes 15 and 17 occurs.

As further confirmation of the diagnosis obtained by the invention assay method, various combinations of primers can be employed. Thus, for example, a plurality of sense primers, all derived from a portion of the myl gene upstream of the point at which translocation occurs, will produce, upon amplification, a series of amplified fragments of varying lengths, depending on the distance between the various sense primers employed and the anti-sense primer. If the number of amplified fragments obtained is less than the number of sense primers employed, this would indicate that the 15, 17 translocation occurred at a different point relative to previously analyzed sample. Alternatively, the observation of fewer amplified fragments may indicate that the originally observed amplification products are derived from regions other than the region of interest.

Sense primers contemplated for use in the practice of the present invention include any sequence of at least 15 contiguous nucleotides selected from nucleotide 1–1249 as set forth in Sequence ID No. 1. Preferred primers comprise at least 20 contiguous nucleotides, with primers of about 30 nucleotides or so being most preferred. While the primer sequence can be selected from anywhere within the above-described sequence of 1249 nucleotides set forth in Sequence ID No. 1, it is preferred that the primer sequence be complementary to sequences located at some distance from the translocation break point (so that the same primer will be effective even if the break point varies somewhat from patient-to-patient, and so the amplification product will be of sufficient size to facilitate detection).

Exemplary sense primers which satisfy the above criteria include:

5'GCGGTACCAG-CGCGACTACG-AGGAGAT-3' (SEQ ID NO: 7)

5'-CTCCTTGACA-GCAGCCACAG-TGAGCTCAAG-3' (SEQ ID NO: 8); and the like.

Anti-sense primers used with the above-described sense primers will comprise any sequence of at least 15 contiguous nucleotides selected from nucleotide 1250–3036, as set forth in Sequence ID No. 1. Preferred primers comprise at least 20 contiguous nucleotides, with primers having about 30 nucleotides or so being most preferred. While the primer sequence can be selected from anywhere within the sequence of nearly 2,000 nucleotides set forth at the above-described 3'-end of Sequence ID No. 1, it is preferred that the primer sequence be selected somewhat distant from the translocation break point (so that the same primer will be effective even if the break point varies somewhat from patient-to-patient, and so that the amplification product will be of sufficient size to facilitate detection). An exemplary anti-sense primer is:

5'-GCGGCGGAAG-AAGCCCTTGC-AGCCCTCACA-GG-3' (SEQ ID NO: 9), and the like.

Alternative sense primers which can be used in the practice of the present invention include any sequence of at least 15 contiguous nucleotides selected from nucleotides 1–280 as set forth in Sequence ID No. 3. Preferred primers comprise at least 20 contiguous nucleotides, with primers of about 30 nucleotides or so being most preferred. It is preferred that the primer sequence be selected somewhat distant from the translocation break point (so that the same primer will be effective even if the break point varies somewhat from patient-to-patient, and so that the amplification product will be of sufficient size to facilitate detection). An exemplary sense primer which satisfied the above criteria is:

5'-AGACTGTCTG-CCTCCCTTCT-GACTG-3' (SEQ ID NO: 10), and the like.

Anti-sense primer used with the above-described sense primer will comprise any sequence of at least 15 contiguous nucleotides selected from nucleotides 1264–2155 as set forth in Sequence ID No. 5. Since the myl gene produces a plurality of expression products (via alternate splicing), anti-sense primer will preferably be derived from at least 15 contiguous nucleotides selected from nucleotides 1264–1334 as set forth in Sequence ID No. 5. While primers derived from further downstream of nucleotide 1334 would successfully amplify translocation products of the myl-1 gene, it is possible that other translocation products (e.g., derived from the myl-2, myl-3, etc. variants of myl) would not be identified with such a primer. Preferred primers comprise at least 20 contiguous nucleotides, which primers of about 30 nucleotides or so being most preferred. It is preferred that the primer sequence be selected somewhat distant from the translocation break point (so that the same primer will be effective even if the break point varies somewhat from patient-to-patient, and so that the amplification product will be of sufficient size to facilitate detection). An exemplary anti-sense primer which satisfies the above criteria is:

5'-CAGGTCAACG-TCAATAGGGT-CCCTG-3' (SEQ ID NO: 11), and the like.

Single-stranded nucleic acid sequences contemplated for use in the practice of the present invention can be derived from the mononuclear cell fraction of the bone marrow cells, blood cells, and the like, of the patient, and include mRNA (or total RNA), which can be amplified, for example by the transcription-based amplification system (TAS) amplification reaction or by the self-sustained sequence replication system (3SR) amplification reaction. Alternatively, RNA obtained from the patient can be copied to produce cDNA, which can be amplified, for example, by the polymerase chain reaction (PCR).

Amplification reactions have been thoroughly described in the scientific literature, and are well within the skill of the artisan. Reference can be made to numerous publications for additional guidance.

See, for example, PCT Publication WO 88/10315 with respect to the transcription-based amplification system (TAS) amplification reaction, or European Patent Application No. 0 373 960 with respect to the self-sustained sequence replication system (3SR) amplification reaction. See, for example, Kumar, in *Technique—A Journal of Methods in Cell and Molecular Biology.* 1:133–152 (1989) with respect to amplification employing the polymerase chain reaction (PCR). See also the detailed protocol set forth in the examples which follows.

The amplified sequences can be detected in a variety of ways. For example, amplified DNA can be size fractionated employing standard techniques for the size separation of nucleic acid material, and then the size fractionated material can be assayed for the presence of sequences having appropriate size based on the distance between the primers employed for amplification.

Alternatively, amplified sequences can be detected by hybridizing the amplified sequences with labeled probes. Labeled probes comprise any sequence complementary with the amplified sequence and further modified with (or containing) a detectable group, e.g., an enzyme, radioactive label and the like. The use of radioactively labeled probes is especially preferred when very high levels of sensitivity are desired. High sensitivity will enable detection of even limited occurrences of translocations between chromosome 15 and chromosome 17. High sensitivity will also make it possible to detect amplified product with the need for fewer amplification cycles (thereby reducing the problem of increased background signal caused by non-specific amplification).

The following Experimental Details section is set forth to aid in an understanding of the invention. This section is not intended to, and should not be construed to, limit in any way the invention set forth in the claims which follow thereafter.

EXPERIMENTAL DETAILS

EXAMPLE 1

Materials: The all-trans retinoic acid was supplied by Hoffmann LaRoche, Inc., Nutley, N.J. Dr. Pierre Chambon, INSERM, Strasbourg, France, supplied RAR-α plasmid for analysis of RAR-α (19, 59). Two probes were isolated from the RAR-α plasmid obtained from Dr. Chambon: A PstI-PstI and a EcoRI-SstI cut fragment. A third probe, a PCR amplified fragment from base # 235 to 404 RAR-α, was synthesized from a MAP disclosed in Giguere, et al. (60). However, any RAR-α probe is sufficient for use in this invention.

Clinical protocol: Patients were eligible for this study if they fulfilled morphologic diagnostic criteria of acute promyelocytic leukemia (M3 or M3-variant sub-type) by classic French-American-British (FAB) classification (12). Karotypes were determined on unstimulated cultures of bone marrow after 48 hours by conventional techniques (13). Patients with both newly-diagnosed and relapsed or resistant APL were eligible. Patients were monitored with complete blood and platelet counts. Bone marrow aspirates were performed approximately once per week during induction until complete remission or failure was documented. Conventional response criteria were observed (14).

Patients were treated with all-trans retinoic acid at a dose of 45 mg/m$^2$/day. In contrast to previous studies (10,11), the drug was formulated in soft gelatin capsules. The drug treatment was divided into 2 equal doses administered approximately 6 hours apart. Patients who achieved complete remission received subsequent therapy depending on their prior treatment status.

Northern analysis for RAR-α expression: Using an established technique (18), total cellular mRNA was purified from bone-marrow mononuclear cells separated by Ficoll-Hypaque density centrifugation. Northern blot analysis was performed on the RNA as previously described (6) by electrophoresis on a 1% agarose-formaldehyde gel which was blotted onto reinforced nitrocellulose (Schleicher & Schuell, Keene, N.H.). The obtained filters were hybridized to a 600 base-pair PstI cut human cDNA for RAR-α (19,59) and were washed stringently at 56° C.(6).

Southern analysis for genomic rearrangements of RAR-α: Genomic DNA was isolated from a 4M guanidine isothiocyanate, 5.7M cesium chloride gradient. The ethanol-precipitated genomic DNA was resuspended in Proteinase K (Sigma) (1 mg/mL) in 10 mM TRIS (pH 7.4), 10 mM EDTA, 150 mM NaCl, 0.4% SDS, heated to 65° C. for 20 minutes, digested overnight at 37° C., extracted twice with phenol/chloroform, reprecipitated with ethanol, and stored at 4° C. in a Tris-buffered solution. For Southern blotting, 10 μg of genomic DNA was completely digested for 3 hours with EcoRI or HindIII (2–3 U/μg DNA) (Boehringer Mannheim, Indianapolis, Ind.) and size-fractionated on a 0.8% agarose gel, denatured, renatured, neutralized, and blotted onto nitrocellulose filters (20). The obtained filters were then hybridized to a 640 base-pair EcoRI-SstI cut RAR-α cDNA (19,59) and washed stringently at 55° C. using our previously described technique (21). Autoradiographs were obtained after exposure at −70° C. to XAR film (Kodak) using an intensifying screen.

Abnormal RAR-α detection by Polymerase Chain Reaction (PCR): A microisolation procedure for total RNA, followed by reverse transcription of mRNA and amplification of the cDNA by a specifically primed polymerase chain reaction yields specific CDNA fragments visualized on agarose gels (61–64). This technique has been employed in samples of as few as 100 cells to identify mRNAs for cytokine expression (62). We are using this mRNA phenotyping approach in the analysis of retinoid receptor genes that are unexpressed at the level of total cellular or the more sensitive level possible within poly A+ or RNAse protected RNA. Isolated cells from the patient are homogenized in 4M guanidine thiocyanate containing carrier RNA or glycogen. Aliquots are layered over a CsCl gradient and RNA is purified as described above. Reverse transcription with oligo dT or random hexamer primers with MMLV reverse transcriptase is performed as described (61–64) followed by 40–60 cycles of PCR amplification using primers which are specific for the rearranged myl/RAR-α mRNA. The product is electrophoresed of a NuSieve agarose gel and visualized by ethidium bromide staining. Further sensitivity is provided by Southern blotting and hybridization to myl or RAR-α probes as discussed above.

Protein expression by Western Blot Analysis: Western blotting for the abnormal RAR-α protein product is done by utilizing standard procedures (65,66). Leukemic cells are resuspended in 1 ml of radioimmunoprecipitation (RIPA) buffer (50 nM Tris-HCL pH 7.5, 150 mM NaCl, Approtinin 10 g/ml, 1% Np-40, 0.5% Sodium deoxycholate, 0.1% SDS) and incubated for 30 minutes on ice with vortexing every 5 minutes. Cell debris can be removed by centrifugation of the lysate at 4° C. at 12,000 g in a microfuge. Fifty to 100 μg of protein from each preparation can by subjected to SDS-PAGE electrophoresis and blotted onto Nitrocellulose membrane. Non-specific binding can be blocked with 5% bovine serum albumin (or 5% low fat milk) in PBS. Membranes will be incubated with appropriate antisera for 2 hours at room temperature followed by washing with Tris-saline (0.9% NaCl, 10 nM Tris-HCl pH 7.5; 6 times, 5–7 minutes/each). Membranes will then be incubated with 10 Ci $^{125}$I-protein A for 60 minutes and washed as described above, dried and subjected to autoradiography at −70° C. If the primary Ab does not bind protein A, a secondary Ab, will be added after washing away the primary Ab. $^{125}$I- protein A will then be added and incubated as described.

Protein expression by Immunoprecipitation: Leukemic cells can be lysed in 1 ml of RIPA buffer and the cell lysate prepared as described above. Specific antiserum will then be added to the supernatant and incubated on ice for 2 hours, followed by adding 100 μl of RIPA buffer containing 5 mg preswollen protein A-sepharose (Sigma). If the primary Ab is monoclonal, the swollen Protein A-sepharose will be incubated with a secondary Ab (in RIPA buffer) on ice for 60 minutes, washed 4–5 times gently with ice-cold RIPA before added to the antibody-lysate mixture. This final reaction mixture will be incubated at 0°–4° C. for 1 hour. The immunoprecipitate will be collected by spinning at 4° C. in a microfuge, washed 5 times with ice-cold RIPA buffer, and then dissolved in 50 μl of 1× sample buffer (2% SDS, 10% glycerol, 0.1% bromophenol blue, 5% B-mercaptoethanol, and then subjected to SDS-PAGE electrophoresis. The gels will be fixed with 10% acetic acid, 50% methanol for 30 minutes, soaked with Enlightenin (NEN DuPont) for 30 minutes, and dried with a Bio-Rad gel dryer at 80° C. for 1–2 hours.

The dried gels will be subjected to autoradiography at −70° C.

PreParation of Antibodies: For the isolation of mouse monoclonal antibodies, eight week old mice may be injected interperitoneally with about 50 micrograms of a purified antigenic protein encoding the RAR-α receptor in complete Freud's adjuvant 1:1 volume. Mice will then be boosted, at monthly intervals, with the protein, mixed with incomplete Freund's adjuvant, and bled through the tail vein. On days 4, 3, and 2 prior to fusion, mice will be boosted intravenously with 50 micrograms of the protein in saline. Splenocyteds will then be fused with secreting myeloma cells according to procedures known to those skilled in the art to which this invention pertains. Some time later, hybridoma supernatent will then be screened for binding activity against the antigenic protein by standard techniques.

Human monoclonal antibodies may be produced by isolating β lymphocytes from a patient's blood, transformed with E.B.V. (Epstein Barr Virus) and selected by the specific recognition of the expressed protein encoding the RAR-α receptor. The cells will then be fused with non-secreting myeloma cells according to known procedures. Some time later, hybridoma supernatant will be screened for binding activity against the protein. Positive clones will then be isolated and propagated.

Experimental Results

Patients: Eleven patients with promyelocytic leukemia were treated with all-trans retinoic acid. Nine of the 11 patients exhibited a characteristic karyotypic abnormality, t(15;17). Despite morphologic evidence of M3-leukemia, two patients did not exhibit the translocation using conventional cytogenetic techniques. Three patients (all of whom had received prior chemotherapy) had additional cytogenetic abnormalities.

Clinical response: Nine of the 11 patients achieved complete remission. Seven of the 9 patients in complete remission were technically evaluable for cytogenetic analysis and all 7 revealed a normal karyotype during remission.

The median time to remission by all criteria was 41 days (range, 24 to 53 days). Due to the early nature of this study, long-term remission duration could not be accurately assessed. Currently, the total duration of complete remission ranges from 1.5 to 6+ months. Two patients (one previously untreated and one in first relapse) were removed from the study due to increasing leukocytosis (described below) and were considered clinical failures at that time. Both of these patients subsequently achieved complete remission with conventional chemotherapy.

Hyperleukocytosis syndrome: A previous report suggested that development of a marked increase in the peripheral blood leukocyte count was associated with a poor outcome (11). Four of the 11 patients in this study experienced an elevated leukocyte count greater than 35,000 cells/$mm^3$ following treatment with all-trans retinoic acid. The first two of those cases were removed from the study due to this event, although one of those patients had exhibited morphologic maturation of her peripheral blood leukocytes. The second two patients were continued on treatment throughout the period of leukocytosis. The leukocyte count of the first of these individuals peaked at 43,000 cells/$mm^3$ in the first week before receding. When the leukocyte count in the second patient reached 77,000 cells/$mm^3$, repeated leukaphereses were undertaken to reduce the leukemic cell burden. The leukocyte count in this patient remained above 50,000 cells/$mm^3$ for 3 weeks before receding. Both cases subsequently achieved complete remission with continued therapy and with alteration of the drug dosage.

Morbidity and adverse effects: No patient died during treatment. Although this therapy did not avoid the major complications of leukemia, in most patients these complications were of lesser severity and were more easily managed. Five of the 11 patients required no platelet transfusions whatsoever. Two patients were discharged quite early from the hospital (on days 5 and 11).

All-trans retinoic acid was extremely well-tolerated. The most frequent reaction was headache that occurred several hours after drug ingestion. In most patients, symptomatic relief was obtained with the use of mild analgesics. However, intracranial hypertension was documented in two patients. Additional side-effects (all of mild intensity) included skin rash, nasal congestion, and hypertriglyceridemia. Unlike previous reports (10,11), we did not observe bone pain or hepatic toxicity at the dosage used in this study.

Molecular analysis of retinoic acid receptor-α: Nine patients with APL were evaluated by Northern analysis performed on total cellular RNA. (Due to insufficient RNA yields, 2 early patients could not be evaluated by this technique.) Eight of these 9 patients exhibited aberrant mRNA expression of RAR-α. All 8 patients who displayed the aberrant message for RAR-α by Northern analysis achieved complete remission following treatment with all-trans retinoic acid. Seven of these 8 patients also exhibited the characteristic t(15;17) karyotypic abnormality. However, one patient who had a normal karyotype by conventional cytogenetics was shown to express an abnormal mRNA species for RAR-α on Northern analysis, and this patient also achieved complete remission. Conversely, the single patient with morphologic M3 leukemia who failed treatment with no evidence of myeloid maturation had a normal karyotype by conventional cytogenetics, a normal chromosome 17 by in situ hybridization, and normal RAR-α expression by Northern analysis.

Figure 1B:
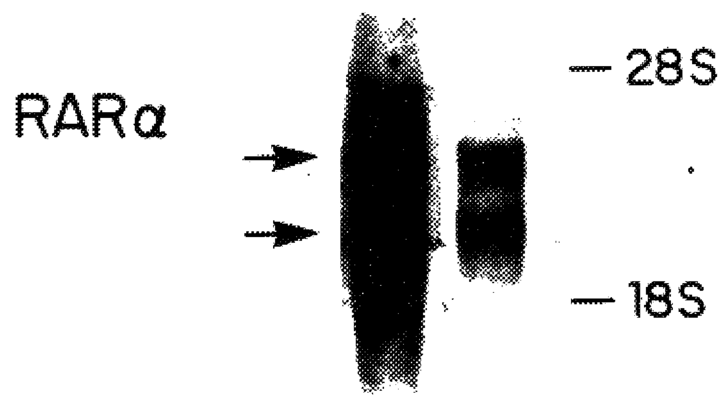

Two predominant patterns of aberrant mRNA expression were observed in APL patients by Northern analysis. These patients are depicted in FIG. 1A wherein the arrows show the two RAR-α bands of normal size, alone with one or two abnormal bands. Furthermore, as a patient achieved complete remission (illustrated in the serial Northern analyses on a representative patient in FIG. 1B), expression of the abnormal RAR-α species markedly decreased. However, in several patients, the abnormal RAR-α message could be detected by Northern analysis despite the achievement of complete remission defined by marrow morphology, peripheral blood counts, and conventional cytogenetics.

Figure 2:
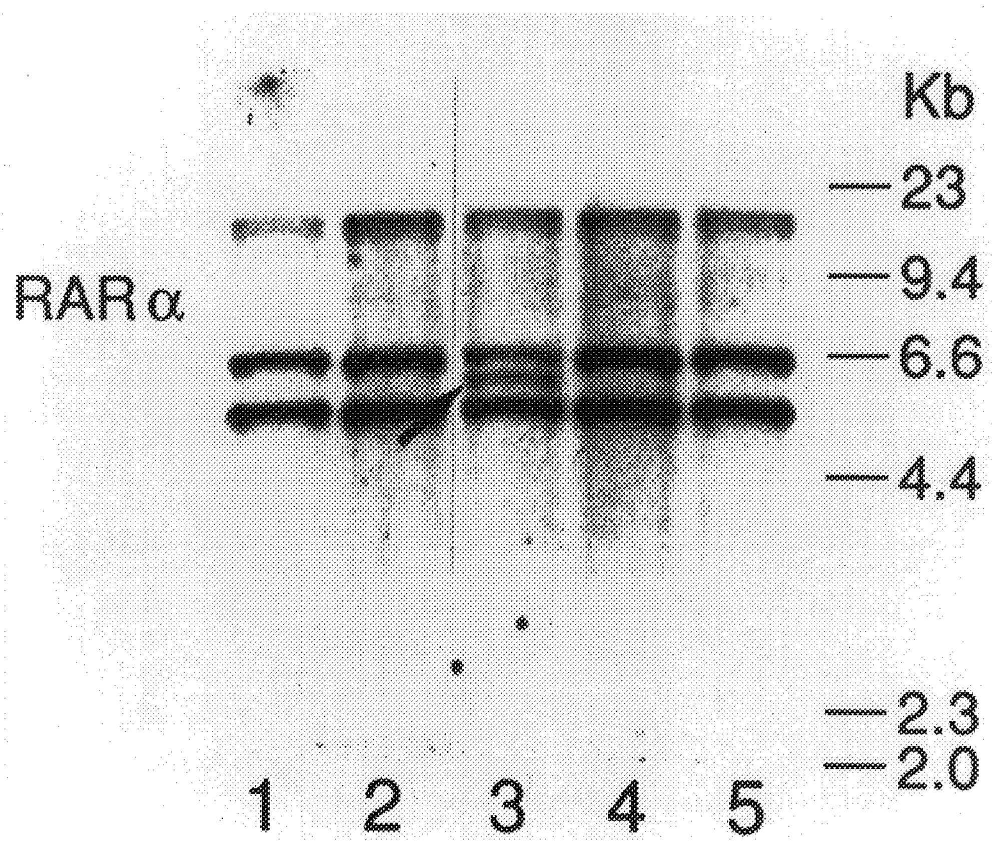
FIG. 2: Southern blot analysis for RAR-α genomic rearrangements in acute promyelocytic leukemia. Indicated lanes represent DNA extracted from human placenta as a control (Lane 1), HL-60 cells (Lane 2), Patient 7 (Lane 3), Patient 6 (Lane 4), and Patient 9 (Lane 5). The arrow in Lane 3 depicts the presence of an RAR-α rearrangement.

Southern blot analysis documented rearrangements of the RAR-α gene in several APL patients. A representative Southern analysis is depicted in FIG. 2, showing the appearance of a rearranged genomic DNA band in one individual. Each of the patients with acute promyelocytic leukemia depicted in FIG. 2 expressed an abnormal RAR-α mRNA species by Northern analysis. Consistent with other reports (5,8), DNA rearrangements by Southern analysis were not detected in HL-60 cells that are known to lack the (15;17) translocation (FIG. 2, lane 2).

Figure 3:
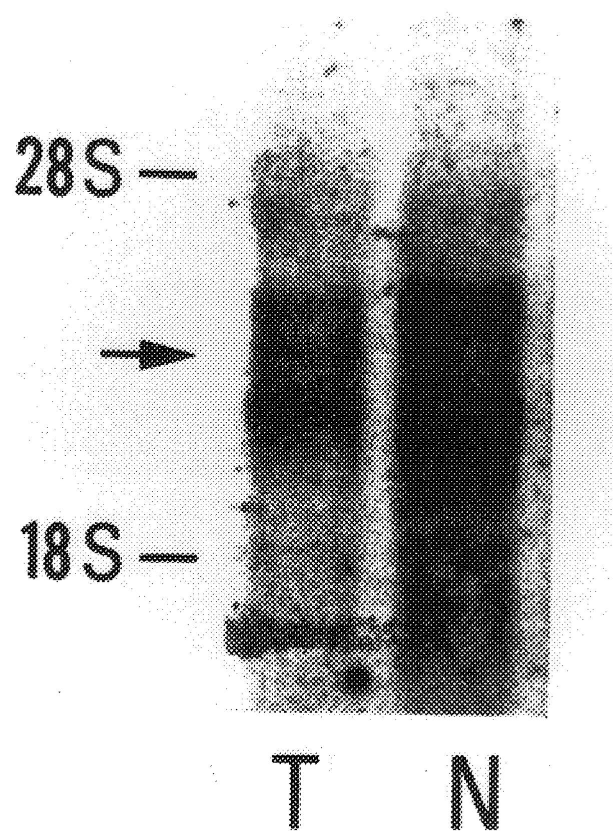
FIG. 3: Northern blot analysis for RAR-α mRNA expression taken from a patient with cancer of the lung. Arrows indicate the position of aberrant expression of the RAR-α mRNA within the tumor (T) of a patient with lung cancer. N refers to this patient's normal lung which has the normal size RAR-α mRNA species.
Figure 5:
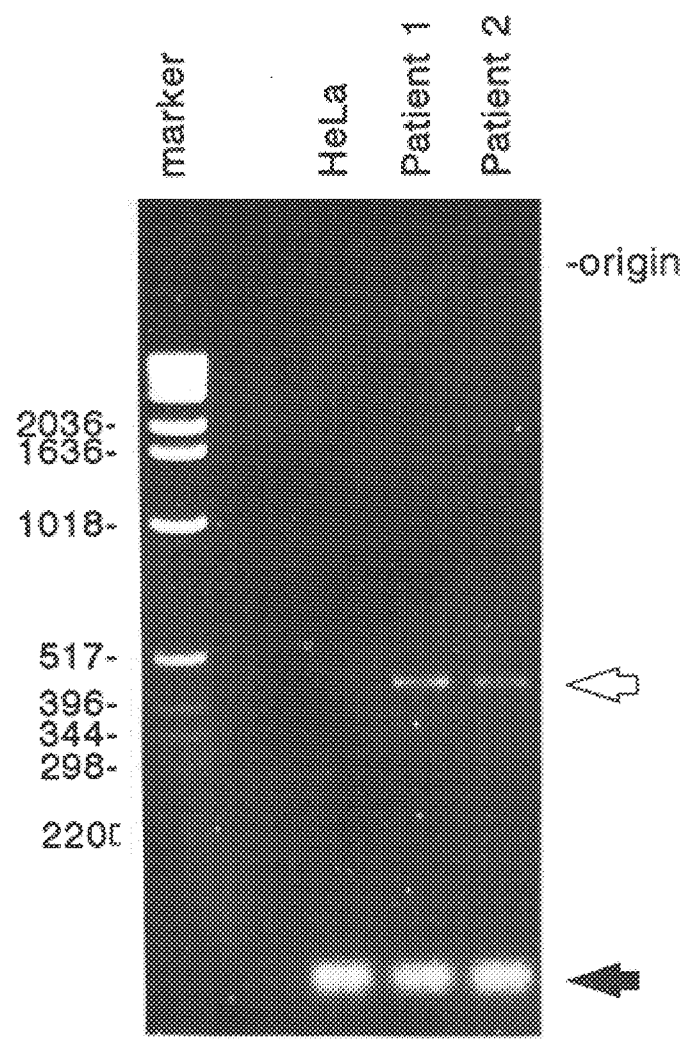
FIG. 5: Photograph of an ethidium bromide-stained gel. The hollow arrow designates amplified product indicative of translocation between chromosome 15 and chromosome 17, while the solid arrow designates unreacted PCR primer.

Northern blot analysis (FIG. 3) of a patient newly diagnosed with lung cancer revealed the presence of an aberrant expression of RAR-α mRNA. The patient's normal lung expressed a normal size RAR-α species. This presents evidence that retinoid compounds can also be used to treat patients with forms of cancer other than APL.

Experimental Discussion

This clinical study confirmed the high effectiveness of all-trans retinoic acid in patients with acute promyelocytic leukemia. Previously, it has been suggested that "every" patient with acute promyelocytic leukemia exhibits the translocation (15;17) if sophisticated cytogenetic techniques are employed (2). In this study, we found one patient with a normal karyotype who expressed the abnormal message for RAR-α, as well as several patients in whom expression of the aberrant message was detected subsequent to karyotypic normalization in remission. Patients who lack the typical karyotypic (9;22) translocation of chronic myelogenous leukemia but who express the consequent bcr/abl fusion product are now well-described in that disorder (33). Thus, it seems likely that presence of the aberrant RAR-α message in acute promyelocytic leukemia can also serve as a new molecular diagnostic marker that is both more sensitive and specific than either light microscopy or conventional cytogenetics. For example, detection of the abnormal transcript may be useful for the evaluation of minimal residual disease in patients with this type of leukemia. Potentially more sensitive techniques, such as polymerase chain reaction amplification of the fusion receptor gene, have been developed by the inventors and should also prove useful. Our study also suggest that the presence of the aberrant RAR-α receptor and the striking clinical responses seen after pharmacologic provision of one of its ligands may be related. In this study, all-trans retinoic acid was extremely effective when the abnormal transcript was expressed; conversely, the drug was ineffective in the single patient who lacked this molecular abnormality. Moreover, minimal cytodifferentiating activity has been observed in liquid cultures of fresh non-M3 myeloid leukemic cells in vitro (27), and no activity has been described in preliminary clinical studies of other myeloblastic leukemias that lack the (15;17) translocation (10,11).

Based on previous reports that suggested the development of leukocytosis presaged a poor outcome (11), we withdrew two of our patients from treatment after their peripheral leukocyte count increased to greater than 35,000 cells/$mm^3$. In at least one of these cases, that decision may have been in error. Two subsequent patients, both of whom showed morphologic evidence of maturation in bone marrow and peripheral blood, were maintained on the drug despite gross elevations of their leukocyte counts. One of those patients was treated with leukapheresis to remove excess leukemic cells and minimize potential morbidity (43). Both of the latter patients subsequently achieved complete remission with continued retinoid treatment. Moreover, the marked increase in S-phase component that we observed in bone marrow cells from one of these patients indicated that this effect resulted from cell division than demargination. The development of extreme leukocytosis may thus indicate cellular proliferation and differentiation of an initially large leukemic cell burden, and this event by itself does not connote therapeutic failure. This phenomenon provides another example that documents the utility of knowing that a patient with APL has (or lacks) the aberrant RAR-α receptor.

Acute promyelocytic leukemia afflicts approximately 600 new patients per year in the United States (50,51). While disease-free survival is somewhat better for this type of leukemia relative to other myeloblastic leukemias, the disease is lethal in more than 60% of patients even at major cancer centers (32,45,52). All-trans retinoic acid is a highly effective drug for inducing complete remission in these patients.

The inventors have shown that the presence of the abnormal RAR-α receptor seems to confer exquisite therapeutic sensitivity to one of its ligands, resulting in cellular maturation and complete clinical remission of leukemia. In addition, the presence of the aberrant RAR-α receptor has been expressed in a patient with lung cancer, documenting the presence of the aberrant receptor in a disease other that APL. Studies have also shown that retinoids have inhibited the growth of breast cancer (67,68). The presence of the aberrant receptor could thus be useful as a diagnostic and therapeutic tool for the detection and treatment of other forms of cancer. Antibodies could be produced that selectively target an expressed protein encoding an RAR-α receptor thereby inhibiting growth of cancer cells.

EXAMPLE 2

Total cellular RNA from patients confirmed to have APL, and from control cells, was extracted (18) from the mononuclear cell fraction of bone marrow cells or peripheral blood cells separated by Ficoll-Hypaque (Pharmacia LKB) sedimentation (70–72). Diagnosis of APL was confirmed according to the FAB cytologocal classification criteria (73) and by the existence of a translocation between chromosome 15 and chromosome 17, as confirmed by karyotype analysis (2, 74–78). Control samples were obtained from healthy individuals, or from a human cell line which does not have the t(15;17), e.g., HeLa cells (79).

The total RNA thus prepared was used for the cDNA as follows. To 1 μg of total RNA, diluted to 10.5 μl with purified water, was added 1 μl of phosphorylated random nucleotide hexamers ($pd(N)_6$ from Pharmacia LKB; 40 ng/μl), then the mixture was heated for 10 minutes at 70° C., and thereafter quickly cooled on ice. To ensure that all the contents of the tube were collected at the bottom of the tube, the tube contents were subjected to a brief centrifugation, then the following additional components were added:

4 μl of 5× Reverse Transcriptase buffer:
 250 mM Tris.HCl, pH 8.3,
 375 mM KCl, and
 15 mM $MgCl_2$;
2 μl of 0.1M dithiothreitol,
1 μl of mixed dNTPs (10 mM each of dATP, dGTP, dCTP, and dTTP, and optionally (if it is desired to monitor the yield of cDNA)
0.5 μl of αdCTP$^{32}$ (3,000 Ci/mmol, 10 μCi/μl).

The resulting mixture was warmed to 37° C. for about 2 minutes, then 1 μl of reverse transcriptase (SuperScript RNaseH$^-$ Reverse Transcriptase from BRL; 200 units/μl) was added, and the mixture held at 37° C. for an additional hour.

The progress of the cDNA preparation can be followed by withdrawing 2 μl of the reaction mixture and subjecting to TCA precipitation. The presence of radioactivity in the precipitate indicates that the radiolabeled dCTP has been incorporated into cDNA. If the RNA preparation used was of good quality, then about 400–500 ng of cDNA should be obtained by the above procedure, although only small amounts of cDNA are required for the following amplification reaction.

The cDNA prepared as described above is then amplified by a PCR reaction as follows. About 0.5–1.0 μl of the cDNA-containing solution (containing in the range of about 10–20 ng of cDNA) was combined with 2.5 μl each of one sense and one anti-sense oligonucleotide primer (oligonucleotide primer stock solution is typically about 10 μM, so that upon dilution, the final concentration of each oligonucleotide in the solution is about 1 μM). The volume of the solution is then adjusted, as needed to a total of 12.5 μl. To this solution is then added 12.5 μl of 2× PCR buffer, which comprises:

134 mM Tris.HCl, pH 8.8,
33.2 mM $(NH_4)_2SO_4$,
20 mM β-mercaptoethanol,
20% dimethylsulfoxide (DMSO),
4 mM $MgCl_2$, and
0.5 mM of each dNTP (i.e., dAPT, dCTP, dTTP, and dGTP).

Finally, 0.25 μl of Taq polymerase (5 units/μl; Cetus) is added, and the resulting mixture subjected to:

1 cycle at 92° C. for 3 minutes;
35 cycles at:
 92° C. for 1 minute, then
 55° C. for 2 minutes, and finally
 72° C. for 3 minutes; and
1 cycle at 70° C. for 10 minutes.

At the end of all 37 PCR cycles, 5 μl of the PCR sample were loaded onto a 2% agarose gel (e.g., SeaKem™ ME agarose, FMC BioProducts, Rockland, Me.) containing about 0.5–1 μg/ml of ethidium bromide (EtBr), along with standard DNA size markers which are readily available, for example, from BRL, Bethesda, Md. The gel was then subjected to electrophoresis conditions, resulting in the gel presented in FIG. 2. In the figure, a band of ~440 bp in length can be seen for samples from both of the confirmed APL patients, but there is no such band observed in control samples, such as the sample obtained from HeLa cells.

For even higher sensitivity than is possible with the above-described stained gel, the products of the amplification reaction can be detected by Southern blot analysis employing a radioactive probe. After the amplification products are separated on gel, as described above, the DNA is transferred to a membrane filter and probed with a suitable radioactively labeled probe. Suitable radioactively labeled probes for use in such analyses can be derived from anywhere within the sequence between the sites where the amplification primers are selected.

REFERENCES

1. Groopman J, Ellman L., *Am. J. Hematol.* 1979; 7:395–408.
2. Larson R. A., Kondo K., Vardiman J. W., Butler A. E., Golomb H. M., Rowley J. D., *AM. J. Med.* 1984; 76:827–841.
3. Lemons R. S., Eilender D., Waldmann R. A., et al., *Genes Chromosomes Cancer* 1990; 2:79–87.
4. Borrow J., Goddard A. D., Sheer D., Solomon E., *Science* 1990; 1249:1577–1580.
5. de The H., Chomienne C., Lanotte M., Degos L., Dejean A., *Nature* 1990; 347:558–651.
6. Miller W. H. Jr., Warrell R. P. Jr., Frankel S., Jakubowski A., Gabrilove J., Muindi J., Dmitrovsky E., *J. Natl. Cancer Inst.* 1990; 82:1932–1933.
7. Chomienne C., Ballerini P., Balitrand N., et al., *Leukemia* 1990; 4:802–807.
8. Longo L., Pandolfi P. P., Biondi A., et al., *J. Exp. Med.* 1990; 172:1571–1575.
9. Collins S. J., Robertson S. J., Mueller L., *Mol. Cell Biol.* 1990; 10:2154–2163.
10. Huang M. E., Ye Y. C., Chai J. R., et al., *Blood* 72: 567–572, 1988.
11. Castaigne S., Chomienne C., Daniel M. T., et al., *Blood* 1990; 76:1704–1709.
12. Bennet J. M., Catovsky D., Daniel M. T., et al., *Ann. Int. Med.* 1985; 103:626–629.
13. Mohamed A. N., Clarkson B. D., Chaganti R. S. K., *Cancer Genet. Cytogenet* 1986; 20:209–222.
14. Cheson B. D., Cassileth P. A., Head D. R., et al., *J. Clin. Oncol.* 1990; 8:813–819.
15. Scheinberg D. A., Tanimoto M., McKenzie S., Strife A., Old L. J., Clarkson B. D., *Leukemia* 1989; 3:440–445.
16. Terstappen L. W. M., Safford M., Loken M. R., *Leukemia* 1990; 4:609–614.
17. Andreeff M., Darzynkiewicz Z., Sharpless T. K., Clarkson B. D., Melamed M. R., *Blood* 1980; 55:282–293.
18. Chirgwin J. M., Przybia A. E., MacDonald R. J., et al., *J. Biochem.* 1979; 18:5294–5299.
19. Petkovich M., Brand N. J., Krust A., et al., *Nature* 1987; 330:444–450.
20. Southern E. M., *J. Mol. Biol.* 1975; 98:503–517.
21. Dmitrovsky E., Murty V. V. V. S., Moy D., et al., *Oncogene* 1990; 5:543–548.
22. English D., Andersen B. R., *J. Immun. Methods* 1974; 5:249–252.
23. Hittelman W. N., Agbor P., Petkovic I., et al., *Blood* 1988; 72:1950–1960.
24. Hittelman W. N., Petkovic I., Agbor P., *Cancer Genetics Cytogenetics* 1988; 30:301–312.
25. Pinkel D., Strauma T., Gray J. W., *Proc. Natl. Acad. Sci.* (*USA*) 1986; 83:2934–2938.
26. Muindi J., Frankel S., Young C. W., Warrell R. P. Jr., *Proc. Am. Soc. Clin. Oncol.* (in press).
27. Chomienne C., Ballerini P., Balitrand, et al., Lancet (*letter*) 1989; 2:736–747.
28. Chomienne C., Ballerini P., Balitrand N., et al., *Blood* 1990; 76:1710–1717.
29. Andreeff M., Redner A., Thongprassert S., Eagle B., Steinherz P., Miller D., Melamed M. R., *In Tumor Aneuploidy*, T. Buchner ed. Berlin: Springer-Verlag, 1985: 81–105.
30. Kantarjian H. M., Keating M. J., McCredie K. B., et al., *J. Clin. Oncol.* 1985; 3:793–798.
31. Wallace P. J., *AM. J. Hematol.* 1989; 31:266–268.
32. Stone R. M., Maguire M., Goldberg M. A., Antin J. H., Rosenthal D. S., Mayer R. J., *Blood* 1988; 71:690–696.
33. Tkachuk D. C., Westbrook C. A., Andreeff M., et al., *Science* 1990; 250:559–562.
34. Mangelsdorf D. J., Ong E. S., Dyck J. A., et al., *Nature* 1990; 345:224–229.
35. Miller W. H. Jr., Frankel S. R., Warrell R. P. Jr., Dmitrovsky E., *Clin. Res.* (in press).
36. Herskowitz I., *Nature* 1987; 329:219–222.
37. Pratt M. A. C., Kralova J., McBurney M. W., *Mol. Cell Biol.* 1990; 10:6445–6453.
38. Flynn P. J., Miller W. J., Weisdorf D. J., Arthur D. C., Brunning R., Branda R. F., *Blood* 1983; 62:1211–1217.
39. Nilsson B., Br., *J. Haematol.* 1984; 57:365–371.
40. Daenen S., Vellenga E., van Dobbenburgh O. A., Halie M. R., *Blood* 1986; 67:559–561.
41. Fontana J. A., Rogers J. S., Durham J. P., *Cancer* 1989; 57:209–217.
42. Wijermans P. W., Rebel V. I., Ossenkoppele G. H., Huijens P. C., Langenhuijsen M. M. A. C., *Blood* 1989; 73:800–805.
43. Lichtman M. A. and Rowe J. M., *Blood* 1982; 60:279–283.
44. Lawrence H. J., Conner K., Kelly M. A., Haussler M. R., Wallace P., Bagby G., *Blood* 1987; 69:302–307.
45. Cunningham I., Gee T. S., Reich L. M., Kempin S. J., Naval A. N., Clarkson B. D., *Blood* 1989; 73:1116–1122.
46. Grainick H. R., Tan H. K., *Hum. Pathol.* 1974; 5:661–673.
47. Goldberg M. A., Ginsburg D., Mayer R. J., et al., *Blood* 1987; 69:187–191.
48. Ventura G. J., Hester J. P., Dixon D. O., Khorana S., Keating M. J., *Hematologic Pathol.* 1989; 3:23–28.
49. Rodeghiero F., Avvisati G., Castaman G., Barbui T., Mandelli F., *Blood* 1990; 75:2112–2117.
50. Jones M. E., Saleem A., *Am. J. Med.* 1978; 65:673–677.
51. Cancer Facts and Figures-1990. *American Cancer Society,* Atlanta. 1990; p. 14.
52. Kantarjian H. M., Keating M. J., Walters R. S., et al., *Am. J. Med.* 1986; 80:789–797.
53. Tobler A., Dawson M. I., Koeffler H. P., *J. Clin. Invest.* 1986; 78:303–309.
54. Douer D., Koeffler P. H., *Exp. Cell Res.* 1982; 138:193–198.
55. Breitman T. R., Selonick, S. E., Collins S. J., *Proc. Natl. Acad. Sci.* (*USA*) 1980; 77:2936–2940.
56. Hong W. K., Lippman S. M., Itri L. M., et al., *N. Engl. J. Med.* 1990; 323:795–801.
57. Warrell R. P. Jr, Coonley C. J., Kempin S. J., Myskowski P., Safai B., Itri L. M., *Lancet* (*letter*) 1983; 2:629.
58. Kessler J. F., Meyskens F. L. Jr, Levine N., Lynch P. J., Jones S. E., *Lancet* 1983; 1:1345–1347.
59. Brand, N. J., et al., *Nature* 1988; 332:850–853.
60. Giguere, V., et al., *Nature* 1987; 330:624.
61. Noonan, K. E. and Roinison I. B., *Nucleic Acids Res.* 1988; 16:10366.

62. Gilliland G., Perrin S., Blanchard K., and Bunn F., *Proc. Natl. Acad. Sci.* (*USA*) 1990; 87:2725–2729.

63. Sarkar G. and Sommer S. S., *Science* 1989; 244:331–334.

64. Chelly J., Concordet J. P., Kaplan J. C., and Kahn A., *Proc. Natl. Acad. Sci.* (*USA*) 1989; 86:2617–2621.

65. Towbin H., Staehlin T., and Gordon J., *Proc. Natl. Acad. Sci.* (*USA*) 1979; 76:4350–4354.

66. Laemmli, U. K., *Nature* 1970; 227:680.

67. Lacroix A. and Lippman, M. E., *J. Clin. Inv.* 1980; 65:586–591.

68. Lotan, R., *Cancer Research* 1979; 39:1014–1019.

69. Kumar, R., *Technique* 1989; 1:152.

70. Peper, et al., *J. Lab. and Clin. Med.* 1968; 72:842–848.

71. Fotino, et al., *Ann. Clin. Lab. Sci.* 1971; 1:131–133.

72. Bain, et al., *Transplantation Proceedings* 1972; 4:163–164.

73. Bennet, et al., *Br. J. Haemotol.* 1976; 33:451–455.

74. de Brackeleer, et al., *Cancer Genet. Cytogenet.* 1986; 19:311–319.

75. International System for Human Cytogenetic Nomenclature, in *Cytogenet. Cell Gen.* 21:399–404

76. Rowley, J. D. *Cancer Res.* 1984; 44:3159–3168.

77. Van Den Berghe, et al., *Cancer* 1979; 43:558–562.

78. Zabel, et al., *Proc. Natl. Acad. Sci. USA* 1983; 80:6932–6936.

79. Gey, et al., *Cancer Res.* 1952; 12:264–265.

SUMMARY OF SEOUENCES

Sequence ID No. 1 presents the nucleic acid and deduced amino acid sequences for a myl/RARα fusion product.

Sequence ID No. 2 presents the deduced amino acid sequence for the nucleotide sequence set forth in Sequence ID No. 1.

Sequence ID No. 3 presents the nucleic acid and deduced amino acid sequences of the retinoid acid receptor-α.

Sequence ID No. 4 presents the deduced amino acid sequence for the nucleotide sequence set forth in Sequence ID No. 3.

Sequence ID No. 5 presents the nucleic acid and deduced amino acid sequences for one variant of the myl gene.

Sequence ID No. 6 presents the deduced amino acid sequence for the nucleotide sequence set forth in Sequence ID No. 5.

---

What is claimed is:

1. A method of identifying a subject with acute promyelocytic leukemia resulting from a t(15;17) translocation who will respond to treatment with all-trans retinoic acid comprising steps of:

(a) obtaining a sample which contains nucleic acid from the subject;

(b) contacting nucleic acid from the sample resulted from step (a) with one-or more primers comprising a portion of the t(15;17) translocation under conditions permitting polymerase chain reaction so as to amplify nucleic acid encoding the abnormal retinoic acid receptor-alpha which results from said translocation; and (c) detecting amplified nucleic acid encoding the abnormal retinoic acid receptor-alpha, such that the presence of the nucleic acid indicates that the subject will respond to treatment with all-trans retinoic acid.

2. A method of claim 1, wherein amplified nucleic acid encoding the abnormal retinoic acid receptor-alpha is detected by size fractionation.

3. A method of claim 2, wherein the size fractionation is effected by a pqlyacrylamide or an agarose gel.

4. A method of claim 1, wherein the detection of amplified nucleic acid encoding the abnormal retinoic acid receptor-alpha comprises contacting the amplified nucleic acid encoding the abnormal retinoic acid receptor-alpha with a retinoic acid receptor-alpha probe labeled with a detectable marker under conditions permitting the retinoid acid receptor-alpha probe to hybridize with amplified nucleic acid encoding the abnormal retinoic acid receptor-alpha, detecting hybridization of amplified nucleic acid encoding the abnormal retinoic acid receptor-alpha with the probe, and thereby detecting the presence of nucleic acid encoding the abnormal retinoic acid receptor-alpha.

5. A method of claim 4, wherein the detectable marker is a radiolabelled molecule, a fluorescent molecule, an enzyme, or a ligand.

6. A method of claim 1, wherein the subject's t(15;17) translocation is not detectable by conventional cytogenetic or morphological methodologies.

7. A method of claim 6, wherein amplified nucleic acid encoding the abnormal retinoic acid receptor-alpha is detected by size fractionation.

8. A method of claim 7, wherein the size fractionation is effected by a polyacrylamide or agarose gel.

9. A method of claim 6, wherein the detection of amplified nucleic acid encoding the abnormal retinoic acid receptor-alpha comprises contacting the amplified nucleic acid encoding the abnormal retinoic acid receptor-alpha with a retinoic acid receptor-alpha probe labeled with a detectable marker under conditions permitting the retinoic acid receptor-alpha probe to hybridize with amplified nucleic acid encoding the abnormal retinoic acid receptor-alpha, detecting hybridization of amplified nucleic acid encoding the abnormal retinoic acid receptor-alpha with the probe, and thereby detecting the presence of nucleic acid encoding the abnormal retinoic acid receptor-alpha.

10. A method of claim 9, wherein the detectable marker is a radiolabelled molecule, a fluorescent molecule, an enzyme, or a ligand.

11. A method of identifying a subject with indications of acute promyelocytic leukemia who will not respond to treatment with all-trans retinoic acid comprising steps of:

(a) obtaining a sample which contains nucleic acid from the subject;

(b) contacting nucleic acid from the sample resulted from step (a) with one or more primers comprising a portion of the t(15;17) translocation under conditions permitting polymerase chain reaction so as to amplify nucleic acid encoding the abnormal retinoic acid receptor-alpha which results from said translocation; and (c) detecting amplified nucleic acid encoding the abnormal retinoic acid receptor-alpha, such that the failure to detect the presence of the nucleic acid indicates that the subject will not respond to treatment with all-trans retinoic acid.

12. A method of claim 11, wherein amplified nucleic acid encoding the abnormal retinoic acid receptor-alpha is detected by size fractionation.

13. A method of claim 12, wherein the size fractionation is effected by a polyacrylamide or agarose gel.

14. A method of claim 11, wherein the detection of amplified nucleic acid encoding the abnormal retinoic acid receptor-alpha comprises contacting the amplified nucleic acid encoding the abnormal retinoic acid receptor-alpha with a retinoic acid receptor-alpha probe labeled with a detectable marker under conditions permitting the retinoic acid receptor-alpha probe to hybridize with amplified nucleic acid encoding the abnormal retinoic acid receptor-alpha, detecting hybridization of amplified nucleic acid encoding the abnormal retinoic acid receptor-alpha with the probe, and thereby detecting the presence of nucleic acid encoding the abnormal retinoic acid receptor-alpha.

15. A method of claim 14, wherein the detectable marker is a radiolabelled molecule, a fluorescent molecule, an enzyme, or a ligand.

16. A method of claim 11, wherein the subject's t(15;17) translocation is not detectable by conventional cytogenetic or morphological methodologies.

17. A method of claim 16, wherein amplified nucleic acid encoding the abnormal retinoic acid receptor-alpha is detected by size fractionation.

18. A method of claim 17, wherein the size fractionation is effected by a polyacrylamide or an agarose gel.

19. A method of claim 16, wherein the detection of amplified nucleic acid encoding the abnormal retinoic acid receptor-alpha comprises contacting the amplified nucleic acid encoding the abnormal retinoic acid receptor-alpha with a retinoic acid receptor-alpha probe labeled with a detectable marker under conditions permitting the retinoic acid receptor-alpha probe to hybridize with amplified nucleic acid encoding the abnormal retinoic acid receptor-alpha, detecting hybridization of amplified nucleic acid encoding the abnormal retinoic acid receptor-alpha with the probe, and thereby detecting the presence of nucleic acid encoding the abnormal retinoic acid receptor-alpha.

20. A method of claim 19, wherein the detectable marker is a radiolabelled molecule, a fluorescent molecule, an enzyme, or a ligand.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 3036 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: MYL-RAR ( i x ) FEATURE:
( A ) NAME/KEY: CDS
( B ) LOCATION: 67..2457
( D ) OTHER INFORMATION:

( x i ) SEQUENCE DESCRIPTION: SEQ ID NO:1:

```
CTCCCCTTCA GCTTCTCTTC ACGCACTCCA AGATCTAAAC CGAGAATCGA AACTAAGCTG      60

GGGTCC ATG GAG CCT GCA CCC GCC CGA TCT CCG AGG CCC CAG CAG GAC        108
       Met Glu Pro Ala Pro Ala Arg Ser Pro Arg Pro Gln Gln Asp
        1               5                  10

CCC GCC CGG CCC CAG GAG CCC ACC ATG CCT CCC CCC GAG ACC CCC TCT      156
Pro Ala Arg Pro Gln Glu Pro Thr Met Pro Pro Pro Glu Thr Pro Ser
 15                  20                  25                  30

GAA GGC CGC CAG CCC AGC CCC AGC CCC AGC CCT ACA GAG CGA GCC CCC      204
Glu Gly Arg Gln Pro Ser Pro Ser Pro Ser Pro Thr Glu Arg Ala Pro
                 35                  40                  45

GCT TCG GAG GAG GAG TTC CAG TTT CTG CGC TGC CAG CAA TGC CAG GCG      252
Ala Ser Glu Glu Glu Phe Gln Phe Leu Arg Cys Gln Gln Cys Gln Ala
             50                  55                  60

GAA GCC AAG TGC CCG AAG CTG CTG CCT TGT CTG CAC ACG CTG TGC TCA      300
Glu Ala Lys Cys Pro Lys Leu Leu Pro Cys Leu His Thr Leu Cys Ser
         65                  70                  75

GGA TGC CTG GAG GCG TCG GGC ATG CAG TGC CCC ATC TGC CAG GCG CCC      348
Gly Cys Leu Glu Ala Ser Gly Met Gln Cys Pro Ile Cys Gln Ala Pro
```

-continued

```
      80                            85                            90

TGG   CCC   CTA   GGT   GCA   GAC   ACA   CCC   GCC   CTG   GAT   AAC   GTC   TTT   TTC   GAG      396
Trp   Pro   Leu   Gly   Ala   Asp   Thr   Pro   Ala   Leu   Asp   Asn   Val   Phe   Phe   Glu
95                            100                           105                           110

AGT   CTG   CAG   CGG   CGC   CTG   TCG   GTG   TAC   CGG   CAG   ATT   GTG   GAT   GCG   CAG      444
Ser   Leu   Gln   Arg   Arg   Leu   Ser   Val   Tyr   Arg   Gln   Ile   Val   Asp   Ala   Gln
                        115                           120                           125

GCT   GTG   TGC   ACC   CGC   TGC   AAA   GAG   TCG   GCC   GAC   TTC   TGG   TGC   TTT   GAG      492
Ala   Val   Cys   Thr   Arg   Cys   Lys   Glu   Ser   Ala   Asp   Phe   Trp   Cys   Phe   Glu
                  130                           135                           140

TGC   GAG   CAG   CTC   CTC   TGC   GCC   AAG   TGC   TTC   GAG   GCA   CAC   CAG   TGG   TTC      540
Cys   Glu   Gln   Leu   Leu   Cys   Ala   Lys   Cys   Phe   Glu   Ala   His   Gln   Trp   Phe
            145                           150                           155

CTC   AAG   CAC   GAG   GCC   CGG   CCC   CTA   GCA   GAG   CTG   CGC   AAC   CAG   TCG   GTG      588
Leu   Lys   His   Glu   Ala   Arg   Pro   Leu   Ala   Glu   Leu   Arg   Asn   Gln   Ser   Val
      160                           165                           170

CGT   GAG   TTC   CTG   GAC   GGC   ACC   CGC   AAG   ACC   AAC   AAC   ATC   TTC   TGC   TCC      636
Arg   Glu   Phe   Leu   Asp   Gly   Thr   Arg   Lys   Thr   Asn   Asn   Ile   Phe   Cys   Ser
175                           180                           185                           190

AAC   CCC   AAC   CAC   CGC   ACC   CCT   ACG   CTG   ACC   AGC   ATC   TAC   TGC   CGA   GGA      684
Asn   Pro   Asn   His   Arg   Thr   Pro   Thr   Leu   Thr   Ser   Ile   Tyr   Cys   Arg   Gly
                        195                           200                           205

TGT   TCC   AAG   CCG   CTG   TGC   TGC   TCG   TGC   GCG   CTC   CTT   GAC   AGC   AGC   CAC      732
Cys   Ser   Lys   Pro   Leu   Cys   Cys   Ser   Cys   Ala   Leu   Leu   Asp   Ser   Ser   His
                  210                           215                           220

AGT   GAG   CTC   AAG   TGC   GAC   ATC   AGC   GCA   GAG   ATC   CAG   CAG   CGA   CAG   GAG      780
Ser   Glu   Leu   Lys   Cys   Asp   Ile   Ser   Ala   Glu   Ile   Gln   Gln   Arg   Gln   Glu
            225                           230                           235

GAG   CTG   GAC   GCC   ATG   ACG   CAG   GCG   CTG   CAG   GAG   CAG   GAT   AGT   GCC   TTT      828
Glu   Leu   Asp   Ala   Met   Thr   Gln   Ala   Leu   Gln   Glu   Gln   Asp   Ser   Ala   Phe
      240                           245                           250

GGC   GCG   GTT   CAC   GCG   CAG   ATG   CAC   GCG   GCC   GTC   GGC   CAG   CTG   GGC   CGC      876
Gly   Ala   Val   His   Ala   Gln   Met   His   Ala   Ala   Val   Gly   Gln   Leu   Gly   Arg
255                           260                           265                           270

GCG   CGT   GCC   GAG   ACC   GAG   GAG   CTG   ATC   CGC   GAG   CGC   GTG   CGC   CAG   GTG      924
Ala   Arg   Ala   Glu   Thr   Glu   Glu   Leu   Ile   Arg   Glu   Arg   Val   Arg   Gln   Val
                        275                           280                           285

GTA   GCT   CAC   GTG   CGG   GCT   CAG   GAG   CGC   GAG   CTG   CTG   GAG   GCT   GTG   GAC      972
Val   Ala   His   Val   Arg   Ala   Gln   Glu   Arg   Glu   Leu   Leu   Glu   Ala   Val   Asp
                  290                           295                           300

GCG   CGG   TAC   CAG   CGC   GAC   TAC   GAG   GAG   ATG   GCC   AGT   CGG   CTG   GGC   CGC     1020
Ala   Arg   Tyr   Gln   Arg   Asp   Tyr   Glu   Glu   Met   Ala   Ser   Arg   Leu   Gly   Arg
            305                           310                           315

CTG   GAT   GCT   GTG   CTG   CAG   CGC   ATC   CGC   ACG   GGC   AGC   GCG   CTG   GTG   CAG     1068
Leu   Asp   Ala   Val   Leu   Gln   Arg   Ile   Arg   Thr   Gly   Ser   Ala   Leu   Val   Gln
      320                           325                           330

AGG   ATG   AAG   TGC   TAC   GCC   TCG   GAC   CAG   GAG   GTG   CTG   GAC   ATG   CAC   GGT     1116
Arg   Met   Lys   Cys   Tyr   Ala   Ser   Asp   Gln   Glu   Val   Leu   Asp   Met   His   Gly
335                           340                           345                           350

TTC   CTG   CGC   CAG   GCG   CTC   TGC   CGC   CTG   CGC   CAG   GAG   GAG   CCC   CAG   AGC     1164
Phe   Leu   Arg   Gln   Ala   Leu   Cys   Arg   Leu   Arg   Gln   Glu   Glu   Pro   Gln   Ser
                        355                           360                           365

CTG   CAA   GCT   GCC   GTG   CGC   ACC   GAT   GGC   TTC   GAC   GAG   TTC   AAG   GTG   CGC     1212
Leu   Gln   Ala   Ala   Val   Arg   Thr   Asp   Gly   Phe   Asp   Glu   Phe   Lys   Val   Arg
                  370                           375                           380

CTG   CAG   GAC   CTC   AGC   TCT   TGC   ATC   ACC   CAG   GGG   AAA   GCC   ATT   GAG   ACC     1260
Leu   Gln   Asp   Leu   Ser   Ser   Cys   Ile   Thr   Gln   Gly   Lys   Ala   Ile   Glu   Thr
            385                           390                           395

CAG   AGC   AGC   AGT   TCT   GAA   GAG   ATA   GTG   CCC   AGC   CCT   CCC   TCG   CCA   CCC     1308
Gln   Ser   Ser   Ser   Ser   Glu   Glu   Ile   Val   Pro   Ser   Pro   Pro   Ser   Pro   Pro
```

-continued

```
        400                     405                     410

CCT CTA CCC CGC ATC TAC AAG CCT TGC TTT GTC TGT CAG GAC AAG TCC    1356
Pro Leu Pro Arg Ile Tyr Lys Pro Cys Phe Val Cys Gln Asp Lys Ser
415                 420                     425                 430

TCA GGC TAC CAC TAT GGG GTC AGC GCC TGT GAG GGC TGC AAG GGC TTC    1404
Ser Gly Tyr His Tyr Gly Val Ser Ala Cys Glu Gly Cys Lys Gly Phe
                435                     440                 445

TTC CGC CGC AGC ATC CAG AAG AAC ATG GTG TAC ACG TGT CAC CGG GAC    1452
Phe Arg Arg Ser Ile Gln Lys Asn Met Val Tyr Thr Cys His Arg Asp
            450                     455                 460

AAG AAC TGC ATC ATC AAC AAG GTG ACC CGG AAC CGC TGC CAG TAC TGC    1500
Lys Asn Cys Ile Ile Asn Lys Val Thr Arg Asn Arg Cys Gln Tyr Cys
        465                     470                 475

CGA CTG CAG AAG TGC TTT GAA GTG GGC ATG TCC AAG GAG TCT GTG AGA    1548
Arg Leu Gln Lys Cys Phe Glu Val Gly Met Ser Lys Glu Ser Val Arg
    480                 485                     490

AAC GAC CGA AAC AAG AAG AAG AAG GAG GTG CCC AAG CCC GAG TGC TCT    1596
Asn Asp Arg Asn Lys Lys Lys Lys Glu Val Pro Lys Pro Glu Cys Ser
495                 500                     505                 510

GAG AGC TAC ACG CTG ACG CCG GAG GTG GGG GAG CTC ATT GAG AAG GTG    1644
Glu Ser Tyr Thr Leu Thr Pro Glu Val Gly Glu Leu Ile Glu Lys Val
                515                     520                 525

CGC AAA GCG CAC CAG GAA ACC TTC CCT GCC CTC TGC CAG CTG GGC AAA    1692
Arg Lys Ala His Gln Glu Thr Phe Pro Ala Leu Cys Gln Leu Gly Lys
            530                     535                 540

TAC ACT ACG AAC AAC AGC TCA GAA CAA CGT GTC TCT CTG GAC ATT GAC    1740
Tyr Thr Thr Asn Asn Ser Ser Glu Gln Arg Val Ser Leu Asp Ile Asp
        545                     550                 555

CTC TGG GAC AAG TTC AGT GAA CTC TCC ACC AAG TGC ATC ATT AAG ACT    1788
Leu Trp Asp Lys Phe Ser Glu Leu Ser Thr Lys Cys Ile Ile Lys Thr
    560                 565                     570

GTG GAG TTC GCC AAG CAG CTG CCC GGC TTC ACC ACC CTC ACC ATC GCC    1836
Val Glu Phe Ala Lys Gln Leu Pro Gly Phe Thr Thr Leu Thr Ile Ala
575                 580                     585                 590

GAC CAG ATC ACC CTC CTC AAG GCT GCC TGC CTG GAC ATC CTG ATC CTG    1884
Asp Gln Ile Thr Leu Leu Lys Ala Ala Cys Leu Asp Ile Leu Ile Leu
                595                     600                 605

CGG ATC TGC ACG CGG TAC ACG CCC GAG CAG GAC ACC ATG ACC TTC TCG    1932
Arg Ile Cys Thr Arg Tyr Thr Pro Glu Gln Asp Thr Met Thr Phe Ser
            610                     615                 620

GAC GGG CTG ACC CTG AAC CGG ACC CAG ATG CAC AAC GCT GGC TTC GGC    1980
Asp Gly Leu Thr Leu Asn Arg Thr Gln Met His Asn Ala Gly Phe Gly
        625                     630                 635

CCC CTC ACC GAC CTG GTC TTT GCC TTC GCC AAC CAG CTG CTG CCC CTG    2028
Pro Leu Thr Asp Leu Val Phe Ala Phe Ala Asn Gln Leu Leu Pro Leu
    640                 645                     650

GAG ATG GAT GAT GCG GAG ACG GGG CTG CTC AGC GCC ATC TGC CTC ATC    2076
Glu Met Asp Asp Ala Glu Thr Gly Leu Leu Ser Ala Ile Cys Leu Ile
655                 660                     665                 670

TGC GGA GAC CGC CAG GAC CTG GAG CAG CCG GAC CGG GTG GAC ATG CTG    2124
Cys Gly Asp Arg Gln Asp Leu Glu Gln Pro Asp Arg Val Asp Met Leu
                675                     680                 685

CAG GAG CCG CTG CTG GAG GCG CTA AAG GTC TAC GTG CGG AAG CGG AGG    2172
Gln Glu Pro Leu Leu Glu Ala Leu Lys Val Tyr Val Arg Lys Arg Arg
            690                     695                 700

CCC AGC CGC CCC CAC ATG TTC CCC AAG ATG CTA ATG AAG ATT ACT GAC    2220
Pro Ser Arg Pro His Met Phe Pro Lys Met Leu Met Lys Ile Thr Asp
        705                     710                 715

CTG CGA AGC ATC AGC GCC AAG GGG GCT GAG CGG GTG ATC ACG CTG AAG    2268
Leu Arg Ser Ile Ser Ala Lys Gly Ala Glu Arg Val Ile Thr Leu Lys
```

```
    720                      725                      730

ATG GAG ATC CCG GGC TCC ATG CCG CCT CTC ATC CAG GAA ATG TTG GAG     2316
Met Glu Ile Pro Gly Ser Met Pro Pro Leu Ile Gln Glu Met Leu Glu
735                     740                     745                 750

AAC TCA GAG GGC CTG GAC ACT CTG AGC GGA CAG CCG GGG GGT GGG GGG     2364
Asn Ser Glu Gly Leu Asp Thr Leu Ser Gly Gln Pro Gly Gly Gly Gly
                755                     760                     765

CGG GAC GGG GGT GGC CTG GCC CCC CCG CCA GGC AGC TGT AGC CCC AGC     2412
Arg Asp Gly Gly Gly Leu Ala Pro Pro Pro Gly Ser Cys Ser Pro Ser
            770                     775                     780

CTC AGC CCC AGC TCC AAC AGA AGC AGC CCG GCC ACC CAC TCC CCG         2457
Leu Ser Pro Ser Ser Asn Arg Ser Ser Pro Ala Thr His Ser Pro
        785                     790                     795

TGACCGCCCA CGCCACATGG ACACAGCCCT CGCCCTCCGC CCCGGCTTTT CTCTGCCTTT   2517

CTACCGACCA TGTGACCCCG CACCAGCCCT GCCCCCACCT GCCCTCCCGG GCAGTACTGG   2577

GGACCTTCCC TGGGGGACGG GGAGGGAGGA GGCAGCGACT CCTTGGACAG AGGCCTGGGC   2637

CCTCAGTGGA CTGCCTGCTC CCACAGCCTG GGCTGACGTC AGAGGCCGAG GCCAGGAACT   2697

GAGTGAGGCC CCTGGTCCTG GGTCTCAGGA TGGGTCCTGG GGGCCTCGTG TTCATCAAGA   2757

CACCCCTCTG CCCAGCTCAC CACATCTTCA TCACCAGCAA ACGCCAGGAC TTGGCTCCCC   2817

CATCCTCAGA ACTCACAAGC CATTGCTCCC CAGCTGGGGA ACCTCAACCT CCCCCCTGCC   2877

TCGGTTGGTG ACAGAGGGGG TGGGACAGGG GCGGGGGGTT CCCCCTGTAC ATACCCTGCC   2937

ATACCAACCC CAGGTATTAA TTCTCGCTGG TTTTGTTTTT ATTTTAATTT TTTTGTTTTG   2997

ATTTTTTTAA TAAGAATTTT CATTTTAAGC AAAAAAAAA                          3036
```

( 2 ) INFORMATION FOR SEQ ID NO:2:

( i ) SEQUENCE CHARACTERISTICS:
( A ) LENGTH: 797 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Glu Pro Ala Pro Ala Arg Ser Pro Arg Pro Gln Gln Asp Pro Ala
  1               5                  10                  15

Arg Pro Gln Glu Pro Thr Met Pro Pro Pro Glu Thr Pro Ser Glu Gly
            20                  25                  30

Arg Gln Pro Ser Pro Ser Pro Ser Pro Thr Glu Arg Ala Pro Ala Ser
        35                  40                  45

Glu Glu Glu Phe Gln Phe Leu Arg Cys Gln Gln Cys Gln Ala Glu Ala
    50                  55                  60

Lys Cys Pro Lys Leu Leu Pro Cys Leu His Thr Leu Cys Ser Gly Cys
 65                  70                  75                  80

Leu Glu Ala Ser Gly Met Gln Cys Pro Ile Cys Gln Ala Pro Trp Pro
                 85                  90                  95

Leu Gly Ala Asp Thr Pro Ala Leu Asp Asn Val Phe Phe Glu Ser Leu
            100                 105                 110

Gln Arg Arg Leu Ser Val Tyr Arg Gln Ile Val Asp Ala Gln Ala Val
        115                 120                 125

Cys Thr Arg Cys Lys Glu Ser Ala Asp Phe Trp Cys Phe Glu Cys Glu
    130                 135                 140

Gln Leu Leu Cys Ala Lys Cys Phe Glu Ala His Gln Trp Phe Leu Lys
145                 150                 155                 160
```

-continued

```
His Glu Ala Arg Pro Leu Ala Glu Leu Arg Asn Gln Ser Val Arg Glu
                165                 170                 175

Phe Leu Asp Gly Thr Arg Lys Thr Asn Asn Ile Phe Cys Ser Asn Pro
            180                 185                 190

Asn His Arg Thr Pro Thr Leu Thr Ser Ile Tyr Cys Arg Gly Cys Ser
        195                 200                 205

Lys Pro Leu Cys Cys Ser Cys Ala Leu Leu Asp Ser Ser His Ser Glu
    210                 215                 220

Leu Lys Cys Asp Ile Ser Ala Glu Ile Gln Gln Arg Gln Glu Glu Leu
225                 230                 235                 240

Asp Ala Met Thr Gln Ala Leu Gln Glu Gln Asp Ser Ala Phe Gly Ala
                245                 250                 255

Val His Ala Gln Met His Ala Ala Val Gly Gln Leu Gly Arg Ala Arg
            260                 265                 270

Ala Glu Thr Glu Glu Leu Ile Arg Glu Arg Val Arg Gln Val Val Ala
        275                 280                 285

His Val Arg Ala Gln Glu Arg Glu Leu Leu Glu Ala Val Asp Ala Arg
    290                 295                 300

Tyr Gln Arg Asp Tyr Glu Glu Met Ala Ser Arg Leu Gly Arg Leu Asp
305                 310                 315                 320

Ala Val Leu Gln Arg Ile Arg Thr Gly Ser Ala Leu Val Gln Arg Met
                325                 330                 335

Lys Cys Tyr Ala Ser Asp Gln Glu Val Leu Asp Met His Gly Phe Leu
            340                 345                 350

Arg Gln Ala Leu Cys Arg Leu Arg Gln Glu Glu Pro Gln Ser Leu Gln
        355                 360                 365

Ala Ala Val Arg Thr Asp Gly Phe Asp Glu Phe Lys Val Arg Leu Gln
    370                 375                 380

Asp Leu Ser Ser Cys Ile Thr Gln Gly Lys Ala Ile Glu Thr Gln Ser
385                 390                 395                 400

Ser Ser Ser Glu Glu Ile Val Pro Ser Pro Pro Ser Pro Pro Pro Leu
                405                 410                 415

Pro Arg Ile Tyr Lys Pro Cys Phe Val Cys Gln Asp Lys Ser Ser Gly
            420                 425                 430

Tyr His Tyr Gly Val Ser Ala Cys Glu Gly Cys Lys Gly Phe Phe Arg
        435                 440                 445

Arg Ser Ile Gln Lys Asn Met Val Tyr Thr Cys His Arg Asp Lys Asn
    450                 455                 460

Cys Ile Ile Asn Lys Val Thr Arg Asn Arg Cys Gln Tyr Cys Arg Leu
465                 470                 475                 480

Gln Lys Cys Phe Glu Val Gly Met Ser Lys Glu Ser Val Arg Asn Asp
                485                 490                 495

Arg Asn Lys Lys Lys Lys Glu Val Pro Lys Pro Glu Cys Ser Glu Ser
            500                 505                 510

Tyr Thr Leu Thr Pro Glu Val Gly Glu Leu Ile Glu Lys Val Arg Lys
        515                 520                 525

Ala His Gln Glu Thr Phe Pro Ala Leu Cys Gln Leu Gly Lys Tyr Thr
    530                 535                 540

Thr Asn Asn Ser Ser Glu Gln Arg Val Ser Leu Asp Ile Asp Leu Trp
545                 550                 555                 560

Asp Lys Phe Ser Glu Leu Ser Thr Lys Cys Ile Ile Lys Thr Val Glu
                565                 570                 575

Phe Ala Lys Gln Leu Pro Gly Phe Thr Thr Leu Thr Ile Ala Asp Gln
            580                 585                 590
```

```
Ile Thr Leu Leu Lys Ala Ala Cys Leu Asp Ile Leu Ile Leu Arg Ile
        595                 600                 605

Cys Thr Arg Tyr Thr Pro Glu Gln Asp Thr Met Thr Phe Ser Asp Gly
    610                 615                 620

Leu Thr Leu Asn Arg Thr Gln Met His Asn Ala Gly Phe Gly Pro Leu
625                 630                 635                 640

Thr Asp Leu Val Phe Ala Phe Ala Asn Gln Leu Leu Pro Leu Glu Met
                645                 650                 655

Asp Asp Ala Glu Thr Gly Leu Leu Ser Ala Ile Cys Leu Ile Cys Gly
            660                 665                 670

Asp Arg Gln Asp Leu Glu Gln Pro Asp Arg Val Asp Met Leu Gln Glu
        675                 680                 685

Pro Leu Leu Glu Ala Leu Lys Val Tyr Val Arg Lys Arg Arg Pro Ser
    690                 695                 700

Arg Pro His Met Phe Pro Lys Met Leu Met Lys Ile Thr Asp Leu Arg
705                 710                 715                 720

Ser Ile Ser Ala Lys Gly Ala Glu Arg Val Ile Thr Leu Lys Met Glu
                725                 730                 735

Ile Pro Gly Ser Met Pro Pro Leu Ile Gln Glu Met Leu Glu Asn Ser
            740                 745                 750

Glu Gly Leu Asp Thr Leu Ser Gly Gln Pro Gly Gly Gly Gly Arg Asp
        755                 760                 765

Gly Gly Gly Leu Ala Pro Pro Pro Gly Ser Cys Ser Pro Ser Leu Ser
    770                 775                 780

Pro Ser Ser Asn Arg Ser Ser Pro Ala Thr His Ser Pro
785                 790                 795
```

( 2 ) INFORMATION FOR SEQ ID NO:3:

( i ) SEQUENCE CHARACTERISTICS:
( A ) LENGTH: 2928 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: hRAR ALPHA ( i x ) FEATURE:
( A ) NAME/KEY: CDS
( B ) LOCATION: 103..1488
( D ) OTHER INFORMATION:

( x i ) SEQUENCE DESCRIPTION: SEQ ID NO:3:

```
GCCATCTGGG CCCAGGCCCC ATGCCCCGAG GAGGGGTGGT CTGAAGCCCA CCAGAGCCCC      60

CTGCCAGACT GTCTGCCTCC CTTCTGACTG TGGCCGCTTG GC ATG GCC AGC AAC        114
                                               Met Ala Ser Asn
                                                1

AGC AGC TCC TGC CCG ACA CCT GGG GGC GGG CAC CTC AAT GGG TAC CCG      162
Ser Ser Ser Cys Pro Thr Pro Gly Gly Gly His Leu Asn Gly Tyr Pro
  5                  10                  15                  20

GTG CCT CCC TAC GCC TTC TTC TTC CCC CCT ATG CTG GGT GGA CTC TCC      210
Val Pro Pro Tyr Ala Phe Phe Phe Pro Pro Met Leu Gly Gly Leu Ser
                 25                  30                  35

CCG CCA GGC GCT CTG ACC ACT CTC CAG CAC CAG CTT CCA GTT AGT GGA      258
Pro Pro Gly Ala Leu Thr Thr Leu Gln His Gln Leu Pro Val Ser Gly
             40                  45                  50

TAT AGC ACA CCA TCC CCA GCC ACC ATT GAG ACC CAG AGC AGC AGT TCT      306
```

-continued

```
Tyr Ser Thr Pro Ser Pro Ala Thr Ile Glu Thr Gln Ser Ser Ser Ser
        55                  60                  65

GAA GAG ATA GTG CCC AGC CCT CCC TCG CCA CCC CCT CTA CCC CGC ATC      354
Glu Glu Ile Val Pro Ser Pro Pro Ser Pro Pro Pro Leu Pro Arg Ile
    70                  75                  80

TAC AAG CCT TGC TTT GTC TGT CAG GAC AAG TCC TCA GGC TAC CAC TAT      402
Tyr Lys Pro Cys Phe Val Cys Gln Asp Lys Ser Ser Gly Tyr His Tyr
85                  90                  95                  100

GGG GTC AGC GCC TGT GAG GGC TGC AAG GGC TTC TTC CGC CGC AGC ATC      450
Gly Val Ser Ala Cys Glu Gly Cys Lys Gly Phe Phe Arg Arg Ser Ile
                105                 110                 115

CAG AAG AAC ATG GTG TAC ACG TGT CAC CGG GAC AAG AAC TGC ATC ATC      498
Gln Lys Asn Met Val Tyr Thr Cys His Arg Asp Lys Asn Cys Ile Ile
            120                 125                 130

AAC AAG GTG ACC CGG AAC CGC TGC CAG TAC TGC CGA CTG CAG AAG TGC      546
Asn Lys Val Thr Arg Asn Arg Cys Gln Tyr Cys Arg Leu Gln Lys Cys
        135                 140                 145

TTT GAA GTG GGC ATG TCC AAG GAG TCT GTG AGA AAC GAC CGA AAC AAG      594
Phe Glu Val Gly Met Ser Lys Glu Ser Val Arg Asn Asp Arg Asn Lys
    150                 155                 160

AAG AAG AAG GAG GTG CCC AAG CCC GAG TGC TCT GAG AGC TAC ACG CTG      642
Lys Lys Lys Glu Val Pro Lys Pro Glu Cys Ser Glu Ser Tyr Thr Leu
165                 170                 175                 180

ACG CCG GAG GTG GGG GAG CTC ATT GAG AAG GTG CGC AAA GCG CAC CAG      690
Thr Pro Glu Val Gly Glu Leu Ile Glu Lys Val Arg Lys Ala His Gln
                185                 190                 195

GAA ACC TTC CCT GCC CTC TGC CAG CTG GGC AAA TAC ACT ACG AAC AAC      738
Glu Thr Phe Pro Ala Leu Cys Gln Leu Gly Lys Tyr Thr Thr Asn Asn
            200                 205                 210

AGC TCA GAA CAA CGT GTC TCT CTG GAC ATT GAC CTC TGG GAC AAG TTC      786
Ser Ser Glu Gln Arg Val Ser Leu Asp Ile Asp Leu Trp Asp Lys Phe
        215                 220                 225

AGT GAA CTC TCC ACC AAG TGC ATC ATT AAG ACT GTG GAG TTC GCC AAG      834
Ser Glu Leu Ser Thr Lys Cys Ile Ile Lys Thr Val Glu Phe Ala Lys
    230                 235                 240

CAG CTG CCC GGC TTC ACC ACC CTC ACC ATC GCC GAC CAG ATC ACC CTC      882
Gln Leu Pro Gly Phe Thr Thr Leu Thr Ile Ala Asp Gln Ile Thr Leu
245                 250                 255                 260

CTC AAG GCT GCC TGC CTG GAC ATC CTG ATC CTG CGG ATC TGC ACG CGG      930
Leu Lys Ala Ala Cys Leu Asp Ile Leu Ile Leu Arg Ile Cys Thr Arg
                265                 270                 275

TAC ACG CCC GAG CAG GAC ACC ATG ACC TTC TCG GAC GGG CTG ACC CTG      978
Tyr Thr Pro Glu Gln Asp Thr Met Thr Phe Ser Asp Gly Leu Thr Leu
            280                 285                 290

AAC CGG ACC CAG ATG CAC AAC GCT GGC TTC GGC CCC CTC ACC GAC CTG     1026
Asn Arg Thr Gln Met His Asn Ala Gly Phe Gly Pro Leu Thr Asp Leu
        295                 300                 305

GTC TTT GCC TTC GCC AAC CAG CTG CTG CCC CTG GAG ATG GAT GAT GCG     1074
Val Phe Ala Phe Ala Asn Gln Leu Leu Pro Leu Glu Met Asp Asp Ala
    310                 315                 320

GAG ACG GGG CTG CTC AGC GCC ATC TGC CTC ATC TGC GGA GAC CGC CAG     1122
Glu Thr Gly Leu Leu Ser Ala Ile Cys Leu Ile Cys Gly Asp Arg Gln
325                 330                 335                 340

GAC CTG GAG CAG CCG GAC CGG GTG GAC ATG CTG CAG GAG CCG CTG CTG     1170
Asp Leu Glu Gln Pro Asp Arg Val Asp Met Leu Gln Glu Pro Leu Leu
                345                 350                 355

GAG GCG CTA AAG GTC TAC GTG CGG AAG CGG AGG CCC AGC CGC CCC CAC     1218
Glu Ala Leu Lys Val Tyr Val Arg Lys Arg Arg Pro Ser Arg Pro His
            360                 365                 370

ATG TTC CCC AAG ATG CTA ATG AAG ATT ACT GAC CTG CGA AGC ATC AGC     1266
```

-continued

```
Met Phe Pro Lys Met Leu Met Lys Ile Thr Asp Leu Arg Ser Ile Ser
        375                 380                 385

GCC AAG GGG GCT GAG CGG GTG ATC ACG CTG AAG ATG GAG ATC CCG GGC     1314
Ala Lys Gly Ala Glu Arg Val Ile Thr Leu Lys Met Glu Ile Pro Gly
    390                 395                 400

TCC ATG CCG CCT CTC ATC CAG GAA ATG TTG GAG AAC TCA GAG GGC CTG     1362
Ser Met Pro Pro Leu Ile Gln Glu Met Leu Glu Asn Ser Glu Gly Leu
405                 410                 415                 420

GAC ACT CTG AGC GGA CAG CCG GGG GGT GGG GGG CGG GAC GGG GGT GGC     1410
Asp Thr Leu Ser Gly Gln Pro Gly Gly Gly Gly Arg Asp Gly Gly Gly
                425                 430                 435

CTG GCC CCC CCG CCA GGC AGC TGT AGC CCC AGC CTC AGC CCC AGC TCC     1458
Leu Ala Pro Pro Pro Gly Ser Cys Ser Pro Ser Leu Ser Pro Ser Ser
            440                 445                 450

AAC AGA AGC AGC CCG GCC ACC CAC TCC CCG TGACCGCCCA CGCCACATGG       1508
Asn Arg Ser Ser Pro Ala Thr His Ser Pro
        455                 460

ACACAGCCCT CGCCCTCCGC CCCGGCTTTT CTCTGCCTTT CTACCGACCA TGTGACCCCG    1568

CACCAGCCCT GCCCCCACCT GCCCTCCCGG GCAGTACTGG GGACCTTCCC TGGGGGACGG    1628

GGAGGGAGGA GGCAGCGACT CCTTGGACAG AGGCCTGGGC CCTCAGTGGA CTGCCTGCTC    1688

CCACAGCCTG GGCTGACGTC AGAGGCCGAG GCCAGGAACT GAGTGAGGCC CCTGGTCCTG    1748

GGTCTCAGGA TGGGTCCTGG GGGCCTCGTG TTCATCAAGA CACCCCTCTG CCCAGCTCAC    1808

CACATCTTCA TCACCAGCAA ACGCCAGGAC TTGGCTCCCC CATCCTCAGA ACTCACAAGC    1868

CATTGCTCCC CAGCTGGGGA ACCTCAACCT CCCCCCTGCC TCGGTTGGTG ACAGAGGGGG    1928

TGGGACAGGG GCGGGGGGTT CCCCCTGTAC ATACCCTGCC ATACCAACCC CAGGTATTAA    1988

TTCTCGCTGG TTTTGTTTTT ATTTTAATTT TTTTGTTTTG ATTTTTTTAA TAAGAATTTT    2048

CATTTTAAGC ACATTTATAC TGAAGGAATT TGTGCTGTGT ATTGGGGGGA GCTGGATCCA    2108

GAGCTGGAGG GGGTGGGTCC GGGGGAGGGA GTGGCTCGGA AGGGGCCCCC ACTCTCCTTT    2168

CATGTCCCTG TGCCCCCCAG TTCTCCTCCT CAGCCTTTTC CTCCTCAGTT TTCTCTTTAA    2228

AACTGTGAAG TACTAACTTT CCAAGGCCTG CCTTCCCCTC CCTCCCACTG GAGAAGCCGC    2288

CAGCCCCTTT CTCCCTCTGC CTGACCACTG GGTGTGGACG GTGTGGGGCA GCCCTGAAAG    2348

GACAGGCTCC TGGCCTTGGC ACTTGCCTGC ACCCACCATG AGGCATGGAG CAGGGCAGAG    2408

CAAGGGCCCC GGGACAGAGT TTTCCCAGAC CTGGCTCCTC GGCAGAGCTG CCTCCCGTCA    2468

GGGCCCACAT CATCTAGGCT CCCCAGCCCC CACTGTGAAG GGGCTGGCCA GGGGCCCGAG    2528

CTGCCCCCAC CCCCGGCCTC AGCCACCAGC ACCCCCATAG GGCCCCCAGA CACCACACAC    2588

ATGCGCGTGC GCACACACAC AAACACACAC ACACTGGACA GTAGATGGGC CGACACACAC    2648

TTGGCCCGAG TTCCTCCATT TCCCTGGCCT GCCCCCCACC CCCAACCTGT CCCACCCCCG    2708

TGCCCCCTCC TTACCCCGCA GGACGGGCCT ACAGGGGGGT CTCCCCTCAC CCCTGCACCC    2768

CCAGCTGGGG GAGCTGGCTC TGCCCCGACC TCCTTCACCA GGGGTTGGGG CCCCTTCCCC    2828

TGGAGCCCGT GGGTGCACCT GTTACTGTTG GGCTTTCCAC TGAGATCTAC TGGATAAAGA    2888

ATAAAGTTCT ATTTATTCTA AAAAAAAAAA AAAAAAAAAA                          2928
```

( 2 ) INFORMATION FOR SEQ ID NO:4:

( i ) SEQUENCE CHARACTERISTICS:
- ( A ) LENGTH: 462 amino acids
- ( B ) TYPE: amino acid
- ( D ) TOPOLOGY: linear ( i i ) MOLECULE TYPE: protein (xi) SEQUENCE DESCRIPTION: SEQ ID NO:4:

Met Ala Ser Asn Ser Ser Ser Cys Pro Thr Pro Gly Gly Gly His Leu
1 5 10 15

Asn Gly Tyr Pro Val Pro Pro Tyr Ala Phe Phe Phe Pro Pro Met Leu
20 25 30

Gly Gly Leu Ser Pro Pro Gly Ala Leu Thr Thr Leu Gln His Gln Leu
35 40 45

Pro Val Ser Gly Tyr Ser Thr Pro Ser Pro Ala Thr Ile Glu Thr Gln
50 55 60

Ser Ser Ser Ser Glu Glu Ile Val Pro Ser Pro Pro Ser Pro Pro Pro
65 70 75 80

Leu Pro Arg Ile Tyr Lys Pro Cys Phe Val Cys Gln Asp Lys Ser Ser
85 90 95

Gly Tyr His Tyr Gly Val Ser Ala Cys Glu Gly Cys Lys Gly Phe Phe
100 105 110

Arg Arg Ser Ile Gln Lys Asn Met Val Tyr Thr Cys His Arg Asp Lys
115 120 125

Asn Cys Ile Ile Asn Lys Val Thr Arg Asn Arg Cys Gln Tyr Cys Arg
130 135 140

Leu Gln Lys Cys Phe Glu Val Gly Met Ser Lys Glu Ser Val Arg Asn
145 150 155 160

Asp Arg Asn Lys Lys Lys Lys Glu Val Pro Lys Pro Glu Cys Ser Glu
165 170 175

Ser Tyr Thr Leu Thr Pro Glu Val Gly Glu Leu Ile Glu Lys Val Arg
180 185 190

Lys Ala His Gln Glu Thr Phe Pro Ala Leu Cys Gln Leu Gly Lys Tyr
195 200 205

Thr Thr Asn Asn Ser Ser Glu Gln Arg Val Ser Leu Asp Ile Asp Leu
210 215 220

Trp Asp Lys Phe Ser Glu Leu Ser Thr Lys Cys Ile Ile Lys Thr Val
225 230 235 240

Glu Phe Ala Lys Gln Leu Pro Gly Phe Thr Thr Leu Thr Ile Ala Asp
245 250 255

Gln Ile Thr Leu Leu Lys Ala Ala Cys Leu Asp Ile Leu Ile Leu Arg
260 265 270

Ile Cys Thr Arg Tyr Thr Pro Glu Gln Asp Thr Met Thr Phe Ser Asp
275 280 285

Gly Leu Thr Leu Asn Arg Thr Gln Met His Asn Ala Gly Phe Gly Pro
290 295 300

Leu Thr Asp Leu Val Phe Ala Phe Ala Asn Gln Leu Leu Pro Leu Glu
305 310 315 320

Met Asp Asp Ala Glu Thr Gly Leu Leu Ser Ala Ile Cys Leu Ile Cys
325 330 335

Gly Asp Arg Gln Asp Leu Glu Gln Pro Asp Arg Val Asp Met Leu Gln
340 345 350

Glu Pro Leu Leu Glu Ala Leu Lys Val Tyr Val Arg Lys Arg Arg Pro
355 360 365

Ser Arg Pro His Met Phe Pro Lys Met Leu Met Lys Ile Thr Asp Leu
370 375 380

Arg Ser Ile Ser Ala Lys Gly Ala Glu Arg Val Ile Thr Leu Lys Met
385 390 395 400

Glu Ile Pro Gly Ser Met Pro Pro Leu Ile Gln Glu Met Leu Glu Asn
405 410 415

```
Ser Glu Gly Leu Asp Thr Leu Ser Gly Gln Pro Gly Gly Gly Gly Arg
            420                 425                 430

Asp Gly Gly Gly Leu Ala Pro Pro Pro Gly Ser Cys Ser Pro Ser Leu
        435                 440                 445

Ser Pro Ser Ser Asn Arg Ser Ser Pro Ala Thr His Ser Pro
    450                 455                 460
```

( 2 ) INFORMATION FOR SEQ ID NO:5:

( i ) SEQUENCE CHARACTERISTICS:
( A ) LENGTH: 2155 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: MYL-1

( i x ) FEATURE:
( A ) NAME/KEY: CDS
( B ) LOCATION: 81..1760
( D ) OTHER INFORMATION:

( x i ) SEQUENCE DESCRIPTION: SEQ ID NO:5:

```
CAACTGGCTC ACGCCTCCCC TTCAGCTTCT CTTCACGCAC TCCAAGATCT AAACCGAGAA      60

TCGAAACTAA GCTGGGGTCC ATG GAG CCT GCA CCC GCC CGA TCT CCG AGG       110
                      Met Glu Pro Ala Pro Ala Arg Ser Pro Arg
                        1               5                  10

CCC CAG CAG GAC CCC GCC CGG CCC CAG GAG CCC ACC ATG CCT CCC CCC     158
Pro Gln Gln Asp Pro Ala Arg Pro Gln Glu Pro Thr Met Pro Pro Pro
                15                  20                  25

GAG ACC CCC TCT GAA GGC CGC CAG CCC AGC CCC AGC CCC AGC CCT ACA     206
Glu Thr Pro Ser Glu Gly Arg Gln Pro Ser Pro Ser Pro Ser Pro Thr
            30                  35                  40

GAG CGA GCC CCC GCT TCG GAG GAG GAG TTC CAG TTT CTG CGC TGC CAG     254
Glu Arg Ala Pro Ala Ser Glu Glu Glu Phe Gln Phe Leu Arg Cys Gln
        45                  50                  55

CAA TGC CAG GCG GAA GCC AAG TGC CCG AAG CTG CTG CCT TGT CTG CAC     302
Gln Cys Gln Ala Glu Ala Lys Cys Pro Lys Leu Leu Pro Cys Leu His
    60                  65                  70

ACG CTG TGC TCA GGA TGC CTG GAG GCG TCG GGC ATG CAG TGC CCC ATC     350
Thr Leu Cys Ser Gly Cys Leu Glu Ala Ser Gly Met Gln Cys Pro Ile
 75                  80                  85                  90

TGC CAG GCG CCC TGG CCC CTA GGT GCA GAC ACA CCC GCC CTG GAT AAC     398
Cys Gln Ala Pro Trp Pro Leu Gly Ala Asp Thr Pro Ala Leu Asp Asn
                95                 100                 105

GTC TTT TTC GAG AGT CTG CAG CGG CGC CTG TCG GTG TAC CGG CAG ATT     446
Val Phe Phe Glu Ser Leu Gln Arg Arg Leu Ser Val Tyr Arg Gln Ile
            110                 115                 120

GTG GAT GCG CAG GCT GTG TGC ACC CGC TGC AAA GAG TCG GCC GAC TTC     494
Val Asp Ala Gln Ala Val Cys Thr Arg Cys Lys Glu Ser Ala Asp Phe
        125                 130                 135

TGG TGC TTT GAG TGC GAG CAG CTC CTC TGC GCC AAG TGC TTC GAG GCA     542
Trp Cys Phe Glu Cys Glu Gln Leu Leu Cys Ala Lys Cys Phe Glu Ala
    140                 145                 150

CAC CAG TGG TTC CTC AAG CAC GAG GCC CGG CCC CTA GCA GAG CTG CGC     590
His Gln Trp Phe Leu Lys His Glu Ala Arg Pro Leu Ala Glu Leu Arg
155                 160                 165                 170

AAC CAG TCG GTG CGT GAG TTC CTG GAC GGC ACC CGC AAG ACC AAC AAC     638
Asn Gln Ser Val Arg Glu Phe Leu Asp Gly Thr Arg Lys Thr Asn Asn
                175                 180                 185
```

-continued

```
ATC TTC TGC TCC AAC CCC AAC CAC CGC ACC CCT ACG CTG ACC AGC ATC      686
Ile Phe Cys Ser Asn Pro Asn His Arg Thr Pro Thr Leu Thr Ser Ile
            190                 195                 200

TAC TGC CGA GGA TGT TCC AAG CCG CTG TGC TGC TCG TGC GCG CTC CTT      734
Tyr Cys Arg Gly Cys Ser Lys Pro Leu Cys Cys Ser Cys Ala Leu Leu
        205                 210                 215

GAC AGC AGC CAC AGT GAG CTC AAG TGC GAC ATC AGC GCA GAG ATC CAG      782
Asp Ser Ser His Ser Glu Leu Lys Cys Asp Ile Ser Ala Glu Ile Gln
    220                 225                 230

CAG CGA CAG GAG GAG CTG GAC GCC ATG ACG CAG GCG CTG CAG GAG CAG      830
Gln Arg Gln Glu Glu Leu Asp Ala Met Thr Gln Ala Leu Gln Glu Gln
235                 240                 245                 250

GAT AGT GCC TTT GGC GCG GTT CAC GCG CAG ATG CAC GCG GCC GTC GGC      878
Asp Ser Ala Phe Gly Ala Val His Ala Gln Met His Ala Ala Val Gly
                255                 260                 265

CAG CTG GGC CGC GCG CGT GCC GAG ACC GAG GAG CTG ATC CGC GAG CGC      926
Gln Leu Gly Arg Ala Arg Ala Glu Thr Glu Glu Leu Ile Arg Glu Arg
            270                 275                 280

GTG CGC CAG GTG GTA GCT CAC GTG CGG GCT CAG GAG CGC GAG CTG CTG      974
Val Arg Gln Val Val Ala His Val Arg Ala Gln Glu Arg Glu Leu Leu
        285                 290                 295

GAG GCT GTG GAC GCG CGG TAC CAG CGC GAC TAC GAG GAG ATG GCC AGT     1022
Glu Ala Val Asp Ala Arg Tyr Gln Arg Asp Tyr Glu Glu Met Ala Ser
    300                 305                 310

CGG CTG GGC CGC CTG GAT GCT GTG CTG CAG CGC ATC CGC ACG GGC AGC     1070
Arg Leu Gly Arg Leu Asp Ala Val Leu Gln Arg Ile Arg Thr Gly Ser
315                 320                 325                 330

GCG CTG GTG CAG AGG ATG AAG TGC TAC GCC TCG GAC CAG GAG GTG CTG     1118
Ala Leu Val Gln Arg Met Lys Cys Tyr Ala Ser Asp Gln Glu Val Leu
                335                 340                 345

GAC ATG CAC GGT TTC CTG CGC CAG GCG CTC TGC CGC CTG CGC CAG GAG     1166
Asp Met His Gly Phe Leu Arg Gln Ala Leu Cys Arg Leu Arg Gln Glu
            350                 355                 360

GAG CCC CAG AGC CTG CAA GCT GCC GTG CGC ACC GAT GGC TTC GAC GAG     1214
Glu Pro Gln Ser Leu Gln Ala Ala Val Arg Thr Asp Gly Phe Asp Glu
        365                 370                 375

TTC AAG GTG CGC CTG CAG GAC CTC AGC TCT TGC ATC ACC CAG GGG AAA     1262
Phe Lys Val Arg Leu Gln Asp Leu Ser Ser Cys Ile Thr Gln Gly Lys
    380                 385                 390

GAT GCA GCT GTA TCC AAG AAA GCC AGC CCA GAG GCT GCC AGC ACT CCC     1310
Asp Ala Ala Val Ser Lys Lys Ala Ser Pro Glu Ala Ala Ser Thr Pro
395                 400                 405                 410

AGG GAC CCT ATT GAC GTT GAC CTG CCC GAG GAG GCA GAG AGA GTG AAG     1358
Arg Asp Pro Ile Asp Val Asp Leu Pro Glu Glu Ala Glu Arg Val Lys
                415                 420                 425

GCC CAG GTT CAG GCC CTG GGG CTG GCT GAA GCC CAG CCT ATG GCT GTG     1406
Ala Gln Val Gln Ala Leu Gly Leu Ala Glu Ala Gln Pro Met Ala Val
            430                 435                 440

GTA CAG TCA GTG CCC GGG GCA CAC CCC GTG CCA GTG TAC GCC TTC TCC     1454
Val Gln Ser Val Pro Gly Ala His Pro Val Pro Val Tyr Ala Phe Ser
        445                 450                 455

ATC AAA GGC CCT TCC TAT GGA GAG GAT GTC TCC AAT ACA ACG ACA GCC     1502
Ile Lys Gly Pro Ser Tyr Gly Glu Asp Val Ser Asn Thr Thr Thr Ala
    460                 465                 470

CAG AAG AGG AAG TGC AGC CAG ACC CAG TGC CCC AGG AAG GTC ATC AAG     1550
Gln Lys Arg Lys Cys Ser Gln Thr Gln Cys Pro Arg Lys Val Ile Lys
475                 480                 485                 490

ATG GAG TCT GAG GAG GGG AAG GAG GCA AGG TTG GCT CGG AGC TCC CCG     1598
Met Glu Ser Glu Glu Gly Lys Glu Ala Arg Leu Ala Arg Ser Ser Pro
                495                 500                 505
```

```
GAG CAG CCC AGG CCC AGC ACC TCC AAG GCA GTC TCA CCA CCC CAC CTG      1646
Glu Gln Pro Arg Pro Ser Thr Ser Lys Ala Val Ser Pro Pro His Leu
            510                 515                 520

GAT GGA CCG CCT AGC CCC AGG AGC CCC GTC ATA GGA AGT GAG GTC TTC      1694
Asp Gly Pro Pro Ser Pro Arg Ser Pro Val Ile Gly Ser Glu Val Phe
        525                 530                 535

CTG CCC AAC AGC AAC CAC GTG GCC AGT GGC GCC GGG GAG GCA GGT AGG      1742
Leu Pro Asn Ser Asn His Val Ala Ser Gly Ala Gly Glu Ala Gly Arg
    540                 545                 550

GAG AGG AAC GCG TTG TGG TGATCAGCAG CTCGGAAGAC TCAGATGCCG             1790
Glu Arg Asn Ala Leu Trp
555                 560

AAAACTCGTC CTCCCGAGAG CTGGATGACA GCAGCAGTGA GTCCAGTGAC CTCCAGCTGG    1850

AAGGCCCCAG CACCCTCAGG GTCCTGGACG AGAACCTTGC TGACCCCCAA GCAGAAGACA    1910

GACCTCTGGT TTTCTTTGAC CTCAAGATTG ACAATGAAAG TGGGTTCTCC TGGGGCTACC    1970

CCCACCCCTT TCTAATTTAG TCTCTGAGTC CCAAAAAGAA GTGCAGGCAG AGCCATCTGC    2030

CAGGCCCAGG AGAGCTCTGA GCTCTGGCCA ACAACTGCAG CCAGGCTGGG CAGAGCACTC    2090

CGGCTCACCT GGGCTCCTGG CGTGTCATTT GCTGGCTTGA ATAAAGATGT CCGCCTTAAA    2150

AAAAA                                                                2155
```

( 2 ) INFORMATION FOR SEQ ID NO:6:

( i ) SEQUENCE CHARACTERISTICS:
( A ) LENGTH: 560 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met Glu Pro Ala Pro Ala Arg Ser Pro Arg Pro Gln Gln Asp Pro Ala
  1               5                  10                  15

Arg Pro Gln Glu Pro Thr Met Pro Pro Pro Glu Thr Pro Ser Glu Gly
            20                  25                  30

Arg Gln Pro Ser Pro Ser Pro Ser Pro Thr Glu Arg Ala Pro Ala Ser
        35                  40                  45

Glu Glu Glu Phe Gln Phe Leu Arg Cys Gln Gln Cys Gln Ala Glu Ala
    50                  55                  60

Lys Cys Pro Lys Leu Leu Pro Cys Leu His Thr Leu Cys Ser Gly Cys
 65                  70                  75                  80

Leu Glu Ala Ser Gly Met Gln Cys Pro Ile Cys Gln Ala Pro Trp Pro
                 85                  90                  95

Leu Gly Ala Asp Thr Pro Ala Leu Asp Asn Val Phe Phe Glu Ser Leu
            100                 105                 110

Gln Arg Arg Leu Ser Val Tyr Arg Gln Ile Val Asp Ala Gln Ala Val
        115                 120                 125

Cys Thr Arg Cys Lys Glu Ser Ala Asp Phe Trp Cys Phe Glu Cys Glu
    130                 135                 140

Gln Leu Leu Cys Ala Lys Cys Phe Glu Ala His Gln Trp Phe Leu Lys
145                 150                 155                 160

His Glu Ala Arg Pro Leu Ala Glu Leu Arg Asn Gln Ser Val Arg Glu
                165                 170                 175

Phe Leu Asp Gly Thr Arg Lys Thr Asn Asn Ile Phe Cys Ser Asn Pro
            180                 185                 190

Asn His Arg Thr Pro Thr Leu Thr Ser Ile Tyr Cys Arg Gly Cys Ser
```

```
                195                     200                     205

Lys Pro Leu Cys Cys Ser Cys Ala Leu Leu Asp Ser Ser His Ser Glu
    210                 215                     220

Leu Lys Cys Asp Ile Ser Ala Glu Ile Gln Gln Arg Gln Glu Glu Leu
225                     230                     235                 240

Asp Ala Met Thr Gln Ala Leu Gln Glu Gln Asp Ser Ala Phe Gly Ala
                245                     250                     255

Val His Ala Gln Met His Ala Ala Val Gly Gln Leu Gly Arg Ala Arg
            260                     265                     270

Ala Glu Thr Glu Glu Leu Ile Arg Glu Arg Val Arg Gln Val Val Ala
        275                     280                     285

His Val Arg Ala Gln Glu Arg Glu Leu Leu Glu Ala Val Asp Ala Arg
    290                     295                     300

Tyr Gln Arg Asp Tyr Glu Glu Met Ala Ser Arg Leu Gly Arg Leu Asp
305                     310                     315                 320

Ala Val Leu Gln Arg Ile Arg Thr Gly Ser Ala Leu Val Gln Arg Met
                325                     330                     335

Lys Cys Tyr Ala Ser Asp Gln Glu Val Leu Asp Met His Gly Phe Leu
            340                     345                     350

Arg Gln Ala Leu Cys Arg Leu Arg Gln Glu Glu Pro Gln Ser Leu Gln
        355                     360                     365

Ala Ala Val Arg Thr Asp Gly Phe Asp Glu Phe Lys Val Arg Leu Gln
    370                     375                     380

Asp Leu Ser Ser Cys Ile Thr Gln Gly Lys Asp Ala Ala Val Ser Lys
385                     390                     395                 400

Lys Ala Ser Pro Glu Ala Ala Ser Thr Pro Arg Asp Pro Ile Asp Val
                405                     410                     415

Asp Leu Pro Glu Glu Ala Glu Arg Val Lys Ala Gln Val Gln Ala Leu
            420                     425                     430

Gly Leu Ala Glu Ala Gln Pro Met Ala Val Val Gln Ser Val Pro Gly
        435                     440                     445

Ala His Pro Val Pro Val Tyr Ala Phe Ser Ile Lys Gly Pro Ser Tyr
    450                     455                     460

Gly Glu Asp Val Ser Asn Thr Thr Thr Ala Gln Lys Arg Lys Cys Ser
465                     470                     475                 480

Gln Thr Gln Cys Pro Arg Lys Val Ile Lys Met Glu Ser Glu Glu Gly
                485                     490                     495

Lys Glu Ala Arg Leu Ala Arg Ser Ser Pro Glu Gln Pro Arg Pro Ser
            500                     505                     510

Thr Ser Lys Ala Val Ser Pro Pro His Leu Asp Gly Pro Pro Ser Pro
        515                     520                     525

Arg Ser Pro Val Ile Gly Ser Glu Val Phe Leu Pro Asn Ser Asn His
    530                     535                     540

Val Ala Ser Gly Ala Gly Glu Ala Gly Arg Glu Arg Asn Ala Leu Trp
545                     550                     555                 560
```

( 2 ) INFORMATION FOR SEQ ID NO:7:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:

( B ) CLONE: MYL-RAR ( x i ) SEQUENCE DESCRIPTION: SEQ ID NO:7:

GCGGTACCAG CGCGACTACG AGGAGAT 27

( 2 ) INFORMATION FOR SEQ ID NO:8:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: MYL-RAR ( x i ) SEQUENCE DESCRIPTION: SEQ ID NO:8:

CTCCTTGACA GCAGCCACAG TGAGCTCAAG 30

( 2 ) INFORMATION FOR SEQ ID NO:9:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: MYL-RAR ( x i ) SEQUENCE DESCRIPTION: SEQ ID NO:9:

GCGGCGGAAG AAGCCCTTGC AGCCCTCACA GG 32

( 2 ) INFORMATION FOR SEQ ID NO:10:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:10:

AGACTGTCTG CCTCCCTTCT GACTG 25

( 2 ) INFORMATION FOR SEQ ID NO:11:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:11:

CAGGTCAACG TCAATAGGGT CCCTG 25